(12) United States Patent
Scarborough

(10) Patent No.: US 7,284,447 B2
(45) Date of Patent: *Oct. 23, 2007

(54) APPARATUS AND METHOD FOR TESTING WELD INTEGRITY

(75) Inventor: Randall L. Scarborough, Carencrow, LA (US)

(73) Assignee: S & H Fabrication, Inc., Scott, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/047,127

(22) Filed: Jan. 31, 2005

(65) Prior Publication Data

US 2005/0204826 A1  Sep. 22, 2005

Related U.S. Application Data

(63) Continuation-in-part of application No. 10/365,105, filed on Feb. 12, 2003, now Pat. No. 6,848,322.

(51) Int. Cl.
*G01N 3/20* (2006.01)

(52) U.S. Cl. ........................................ 73/850

(58) Field of Classification Search .............. 73/809, 73/850

See application file for complete search history.

(56) References Cited

U.S. PATENT DOCUMENTS

| 4,020,680 A | * | 5/1977 | Mehdizadeh et al. .......... 73/86 |
| 4,502,338 A | * | 3/1985 | Smith et al. .................. 73/819 |
| 4,676,110 A | * | 6/1987 | Hodo et al. ................... 73/809 |
| 4,864,866 A | * | 9/1989 | Hardy et al. .................. 73/831 |
| 5,380,393 A | * | 1/1995 | Drabarek et al. ........... 156/358 |

* cited by examiner

*Primary Examiner*—Max Noori
(74) *Attorney, Agent, or Firm*—The Matthews Firm

(57) ABSTRACT

An apparatus and method for testing weld integrity is disclosed which is portable, self-contained, adaptable for field use in most locations, and can verify the integrity of attachment welds. The testing apparatus includes a cylinder or cylinders, attachable to the desired object to be tested on one end and to a cross bar on the other end, support beam or beams which, along with the cylinder or cylinders, support the test apparatus, a supply for pressurized fluid, and a control manifold for flow direction and pressure measurement. The pressurized fluid moves the cylinder shaft creating a load on the test piece. As the fluid pressure increases, the cylinder shafts extend or retract and exert a required load on the test piece. The test piece is then inspected for breakage or damage such as deformation or attachment weld cracking.

31 Claims, 19 Drawing Sheets

APPARATUS AND METHOD FOR TESTING WELD INTEGRITY

CROSS REFERENCE TO RELATED APPLICATIONS

This application is a continuation-in-part of prior application Ser. No. 10/365,105, filed Feb. 12, 2003 now U.S. Pat. No. 6,848,322.

FIELD OF THE INVENTION

The present apparatus relates, generally, to non-destructive testing of weld integrity and strength in the attachment weld of pad eyes and other lifting lugs.

DESCRIPTION OF THE RELATED ART

Presently, the weld integrity of pad eye or other lifting lug welds are only tested by x-rays or liquid penetrant. This testing is at best random and cannot insure the safety or reliability of the pad eyes especially after many cycles. The failure of the pad eyes can cause equipment damage and destruction as well as compromise the safety of workers and by-standers. In particular, when drill string piping is off loaded, from a barge or supply boat, the failure of the pad eyes does cause the loss of human life due to the extreme weight of the pipe and its uncontrolled fall.

Pad eyes and lifting lugs are primarily used as an attachment point for any rigging employed to hoist, transport, or secure heavy equipment. These pad eyes are typically welded either to the equipment or to some device on which the equipment is transported. The strength of these welds cannot be easily tested after they have been manufactured. Usually, the only indication of weakness is discovered upon the complete failure of the attachment weld.

Currently, there are similar approaches to the present device disclosed in other patents. However, there is no prior art for the method or apparatus for testing the pad eye welds. U.S. Pat. No. 4,676,110 issued to James Hodo, et al., discloses a fatigue testing apparatus. However, this apparatus utilizes a method of destructive testing which would render the pad eye useless. Other prior art for pull testing is disclosed in U.S. Pat. Nos. 5,844,142 and 5,918,284, both issued to John Blanch, et al. However, these systems are not portable, are not for larger loads, and are only intended for testing the products during manufacturing. These systems are also used to test the strength for one-time use only products, such as surgical sutures and needles. The pad eye welds must withstand a vast number of loading cycles, with a varied amount of loads, throughout their useful life.

There are other prior art testing tools such as disclosed in U.S. Pat. No. 6,186,011 B1, issued to Pey Min Wung, et al., which tests the failure modes of spot welds on sheet metal. Another testing tool disclosed in U.S. Pat. No. 6,216,531 B1, issued to Joe Zhou, tests the shear strength of adhesive bonded materials. However, both of these inventions are based on pre-manufacture testing, do not consider cyclic loading over the useful life of the product, and cannot be adapted for portability. These testing tools also cannot be adapted to perform testing of finished products or to test the weld integrity before each use.

It is thus a desire to have a testing apparatus which is portable and can quickly and accurately check the integrity of a pad eye and its attachment weld before each field use. The desired apparatus should be portable, self-contained, easily transportable, and environmentally safe in order to test the pad eye welds at almost any location. This testing device should be capable of being hydraulically operated as well as by other available pressurized fluid sources. This device could consist of one or multiple pressurized fluid cylinders depending on the required test loads and the configuration of the apparatus. The effective area of the cylinder piston and the pressure applied to the cylinder would determine the capacity of the apparatus. The fluid pressure is preferably supplied by a hand pump for currently optimum portability; however, other types of pumps could be utilized. A flow manifold would be needed to control the flow direction as well as measure the pressure applied to the cylinder(s). One end of the cylinder(s) would be attached to the same base as is the pad eye or attached to its own base plate. The other end is attached to a cross bar, bridge plate, or similarly functioning member. The cross bar, bridge plate, or similarly functioning member could be further supported by either cylinders or support beams.

BRIEF DESCRIPTION OF THE SEVERAL VIEWS OF THE DRAWING

For a further understanding of the nature of the present device, reference should be had to the following detailed description, taken in conjunction with the accompanying drawings, in which like elements are given the same or analogous reference numbers and wherein.

DETAILED DESCRIPTION OF EMBODIMENTS OF THE INVENTION

Figure 1:
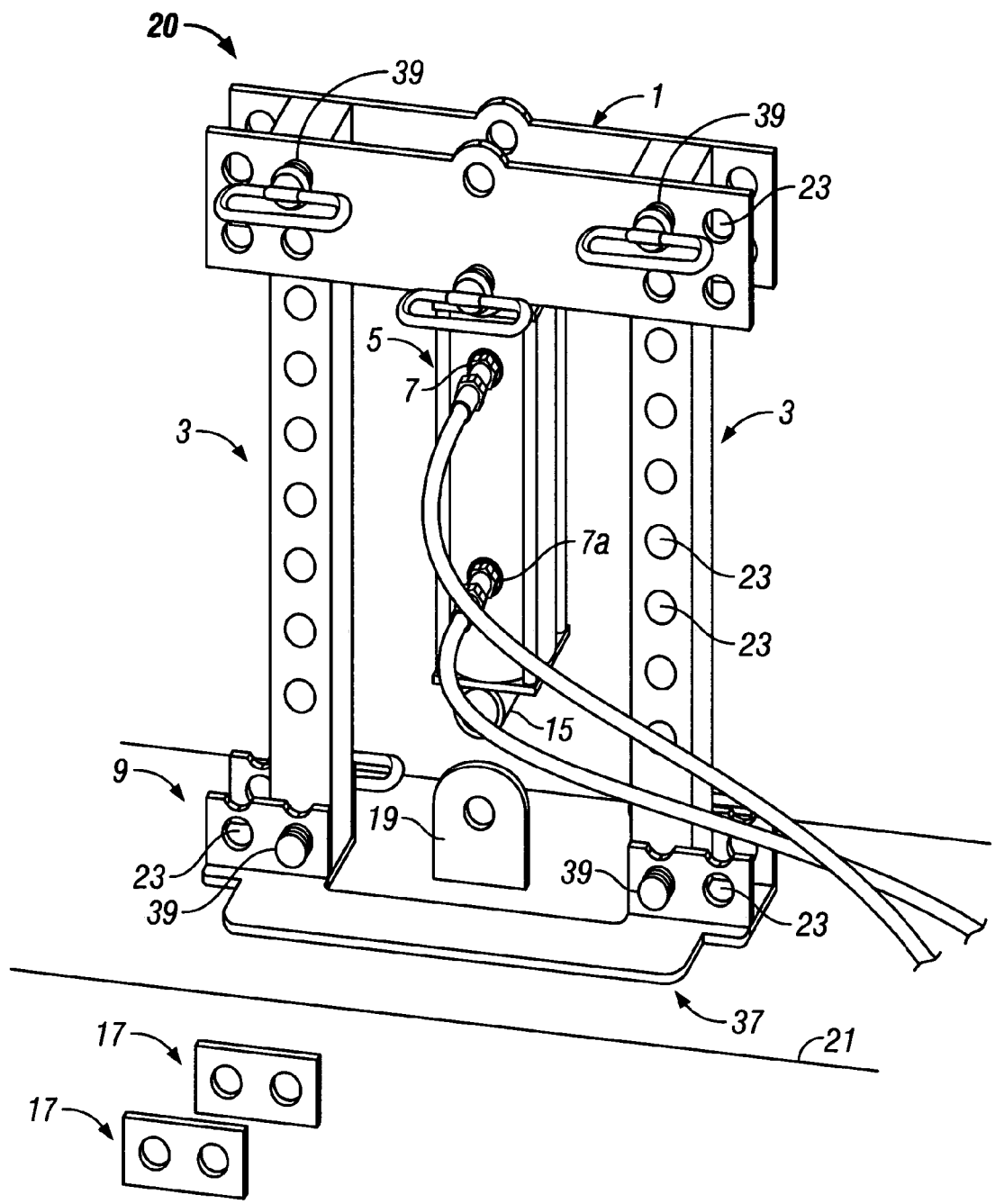
FIG. 1 is a front view assembly drawing of a preferred form of the testing apparatus 20.
Figure 2:
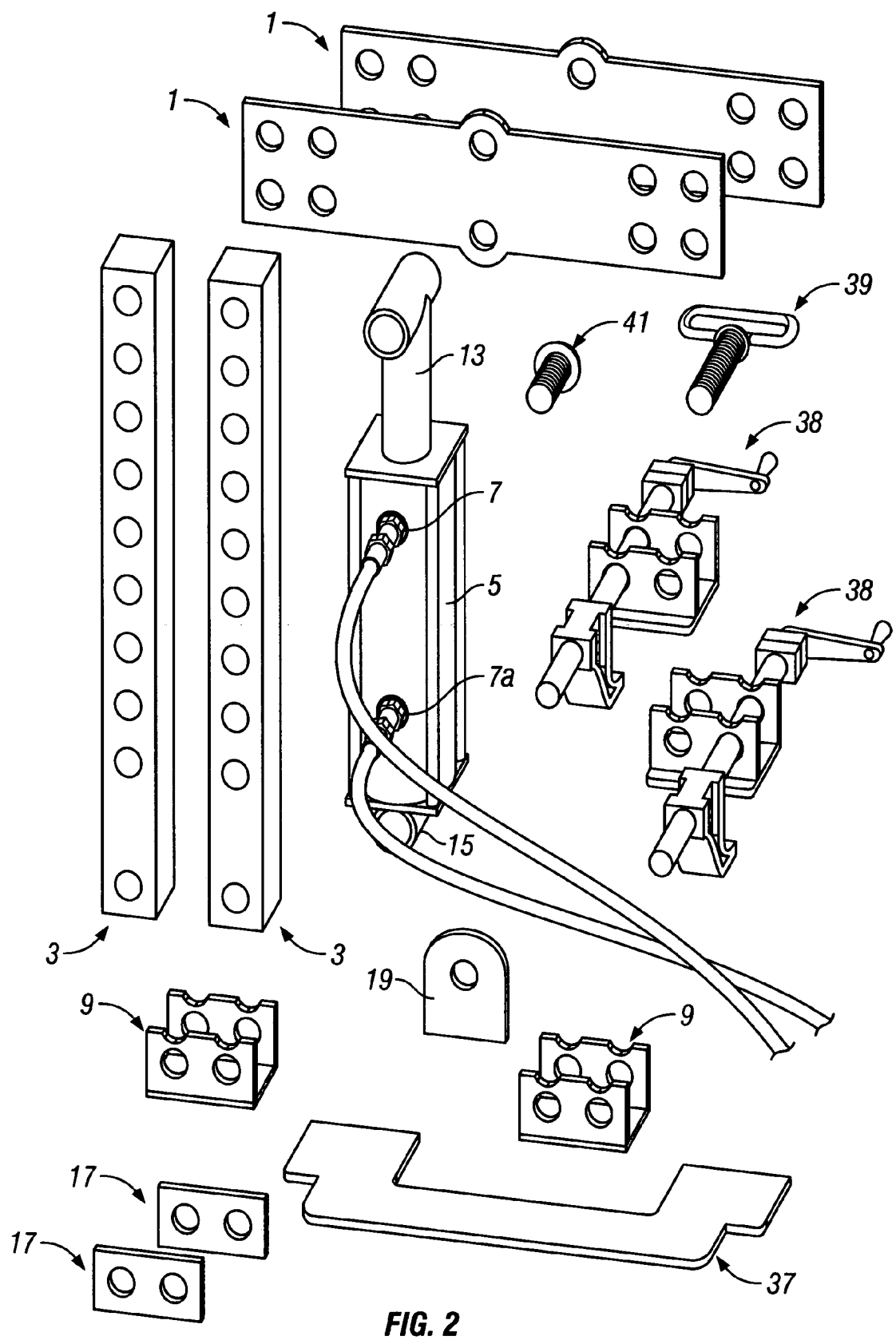
FIG. 2 is a view of FIG. 1 in its disassembled state.

FIG. 1 is an assembly drawing of the present device. FIG. 2 shows the individual components of the testing apparatus 20 which preferably includes the cylinder 5, two bridge plates 1, two support beams 3, one being the right side beam and one being the left side beam, two footings 9 comprised of a right side footing and a left side footing, and two attachment plates 17, FIG. 2.

Figure 1A:
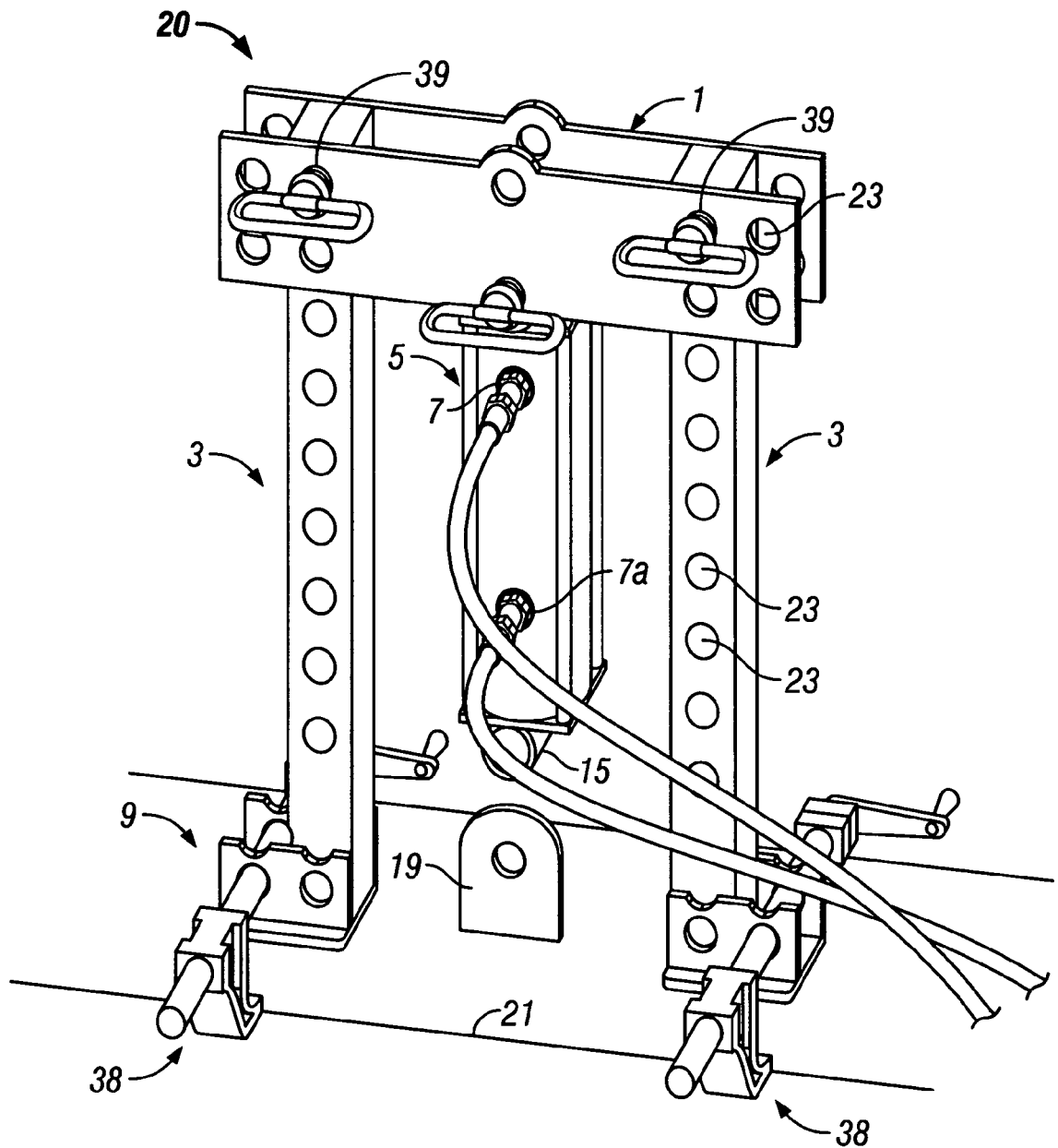
FIG. 1A is another embodiment of FIG. 1 illustrating the option of attachment, of the present apparatus, to the device to be tested, by clamps.

It should be appreciated that the footings 9 and the attachment plates 17 are an illustrative method of attaching the apparatus to the pad eye 19 or lifting lug. Other ways of attachment which provide adequate support and connection can be employed without departing from the scope thereof. The test apparatus can be mounted to a base plate 37 in order to provide support for the test apparatus. As seen in FIG. 1A, it can also be used without the base plate 37 and attached via clamps 38 or other conventional method directly to the base support structure to which the pad eye 19, the lifting lug, or other lifting connection it is attached to.

Figure 7:
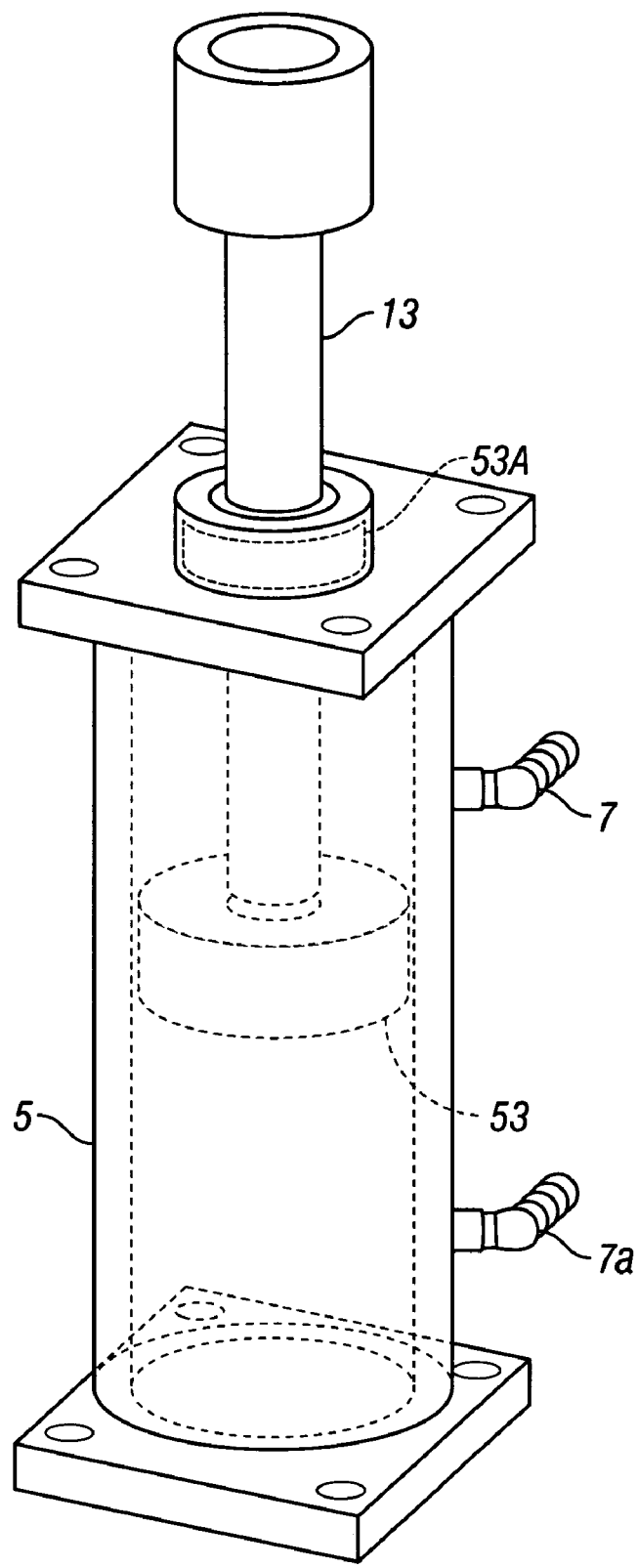
FIG. 7 is a simplified cross sectional representation of the cylinder depicted in FIGS. 1, 2, 3, and 4.

As shown in FIG. 1 and FIG. 2, the cylinder 5 is comprised of a shaft 13 on the topside of the cylinder, an upper 7 and lower 7A cylinder fitting, and a bottom adaptor 15. The internal portion of the cylinder, FIG. 7, is well known to those in the art and typically consists of one or more pistons 53 and o-rings or seals 53A. The said piston 53 is attached to the shaft 13 and will typically move upward, extending the cylinder shaft 13 as pressure is applied through the lower cylinder fitting 7A. When the pressurized fluid is applied through the upper cylinder fitting 7, the piston moves downward and the cylinder shaft 13 retracts. Both the cylinder shaft 13 and the bottom adaptor 15 are adapted to allow connection to a mating part preferably utilizing a pin connection. It should be appreciated that although the present device contemplates primarily pinned connections, other methods of attachment can also be used. Examples of such attachment include, but are not limited to: various threaded fasteners, taper pins, welding, and the like. The figures illustratively show two types of pins 39, 41. However, these pins 39, 41 can be interchanged as well as be substituted by a variety of other attachment methods as mentioned above. The cylinder shaft 13 is sandwiched between and connected, by a pin 39, to the two bridge plates 1. The bottom adaptor 15 is connected by a pin 39 and sandwiched between the attachment plates 17. For the preferred embodiment of the present apparatus, pressure containing hoses are connected to the upper 7 and lower 7A cylinder fittings.

Each of the two bridge plates 1 is preferably substantially identical flat rectangular bars made of steel or a material with similar strength properties. These said bridge plates 1 have a plurality of apertures 23 which are used for the fixed connections between the two bridge plates 1 and the cylinder shaft 13 and the two support beams 3. It should be appreciated that the hole 23 diameter and consequently the diameter of the pin 39 varies in size depending on the load which will be tested and are typically sized by calculation based on the maximum load contemplated. Preferably, there is a plurality of apertures 23 located on the right and left lengthwise ends of the bridge plate 1 and also located substantially symmetrically around the lengthwise and widthwise centers of the said bridge plate 1. Preferably, said apertures 23, located on the right and left lengthwise ends, should be substantially symmetrically located at each end of the bridge plates. Preferably, said apertures 23, at each end of said bridge plate 1, are substantially symmetrically located with respect to said bridge plate 1 and each other. The apertures 23 located approximately midway of both the lengthwise and widthwise centers of said bridge plates 1 are preferably substantially symmetrically located at said midway point. The multiple apertures 23 are used for allowing vertical and horizontal adjustment of the test apparatus. The cylinder shaft 13 is preferably fixedly attached at substantially the lengthwise midpoint of the bridge plate 1 by pin 39. The two bridge plates 1 are fixedly attached at opposing ends, left and right side, and to the outside face of the two support beams 3 by pin 39.

The two support beams 3 are preferably hollow rectangular beams made of steel or a material with similar strength properties. These said support beams 3 have a plurality of apertures 23 on all four faces of the rectangular beam which are used for the fixed connections between the two support beams 3 and the two bridge plates 1 and the two footings 9. It should be appreciated that the hole 23 diameter and consequently the diameter of the pin 39 varies in size depending on the load which will be tested and are typically sized by calculation based on the maximum load contemplated. Preferably, the apertures 23, on each face of the support beams 3, are substantially centered lengthwise on each face of the support beam 3 and are substantially symmetrically spaced from the top of said support beam 3. The multiple apertures 23 are used for allowing vertical and horizontal adjustment of the testing apparatus. The bottom end of the two support beams 3 has a hole on each of the four faces. Preferably, the said apertures 23 are substantially symmetrically located on the lengthwise centerline of each face of the said support beam 3. As described above and shown in FIG. 1, the support beams 3 are fixedly attached near the top end of said support beam 3 sandwiched between the two bridge plates 1 and fixedly attached preferably utilizing the pin 39. The bottom end, of each said support beam 3, is preferably fixedly attached to the two footings 9 by pin 39.

The two footings 9 are preferably comprised of a steel, or a material with similar strength properties, channel bar. Preferably, the two channel sides have matching apertures 23 on each face. Preferably, said hole diameters are substantially symmetrically centered relative to the said channel bar height and substantially symmetrically spaced between the respective apertures centers on each channel wall face. The two footings 9 will preferably be attached by welding to the test apparatus base plate 37 or attached by clamps to the pad eye base plate 21. Preferably, the two footings 9 are substantially horizontally and symmetrically centered on each side of the pad eye 19. This said placement, of the two footings 9, is assured through the substantially symmetric connection of the support beams 3 to bridge plate 1. This said positioning insures that the testing apparatus will provide an approximately equal upward force on the pad eye 19.

The two attachment plates 17 are comprised of two substantially identical pieces of flat steel, or a material with similar strength properties, bar. The attachment plates 17 have a plurality of apertures 23. The hole 23 diameters are substantially centered along the lengthwise centerline of the flat face of the attachment plates 17. The said apertures 23 are further substantially symmetrically located at opposing lengthwise ends of the said attachment plates 17. The attachment plate 17 is fixedly attached on the upper end, by pin 39, to the end of the bottom adaptor 15. The said bottom adaptor 15 is fixedly attached, by pin 39, pinned between the two attachment plates 17. The lower end of said attachment plates 17 is attached to the pad eye 19 by pin 39. The pad eye 19 is sandwiched between the two attachment plates.

Figure 8:
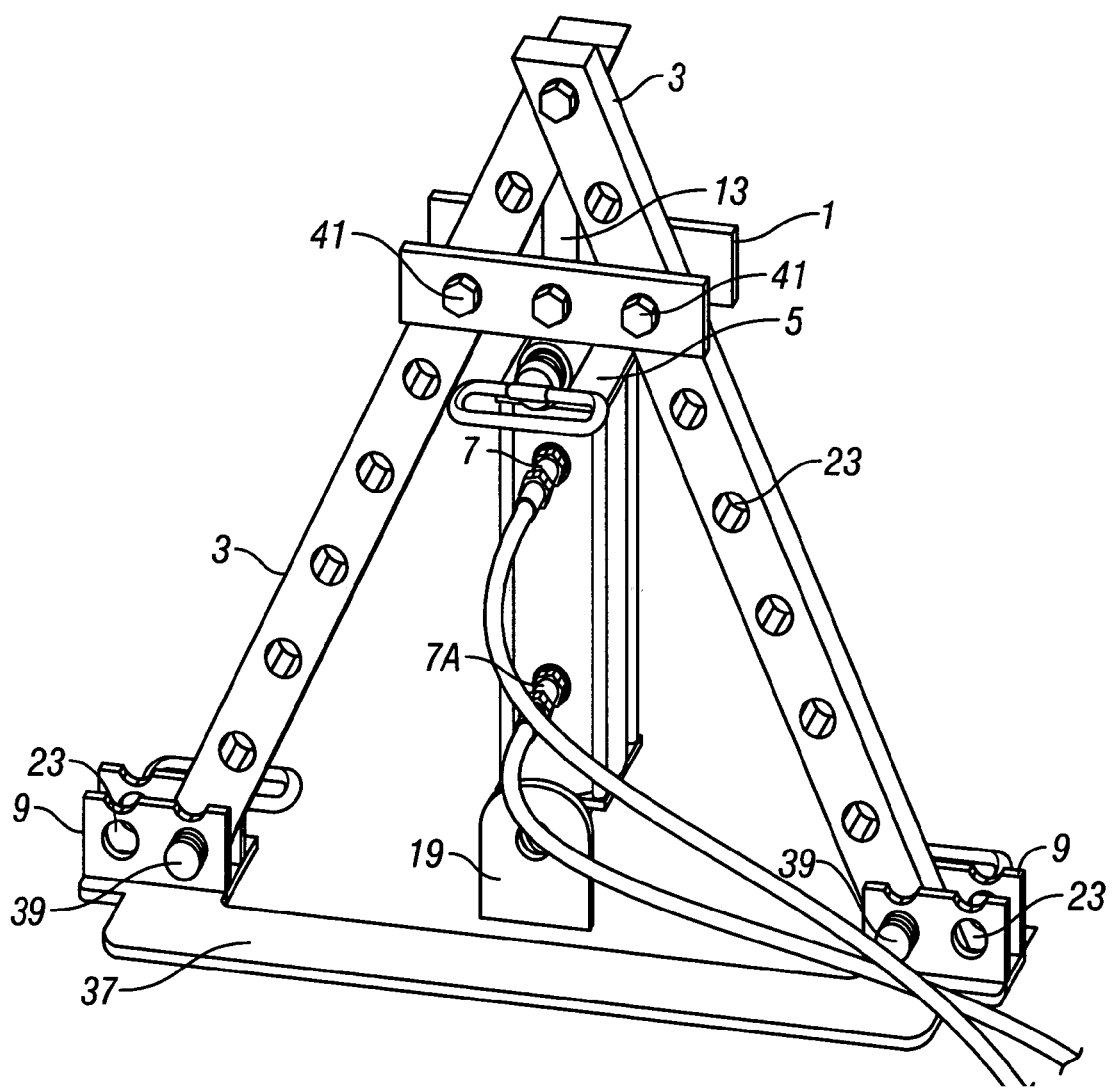
FIG. 8 is a front view assembly drawing of an alternative embodiment of the testing apparatus.
Figure 8A:
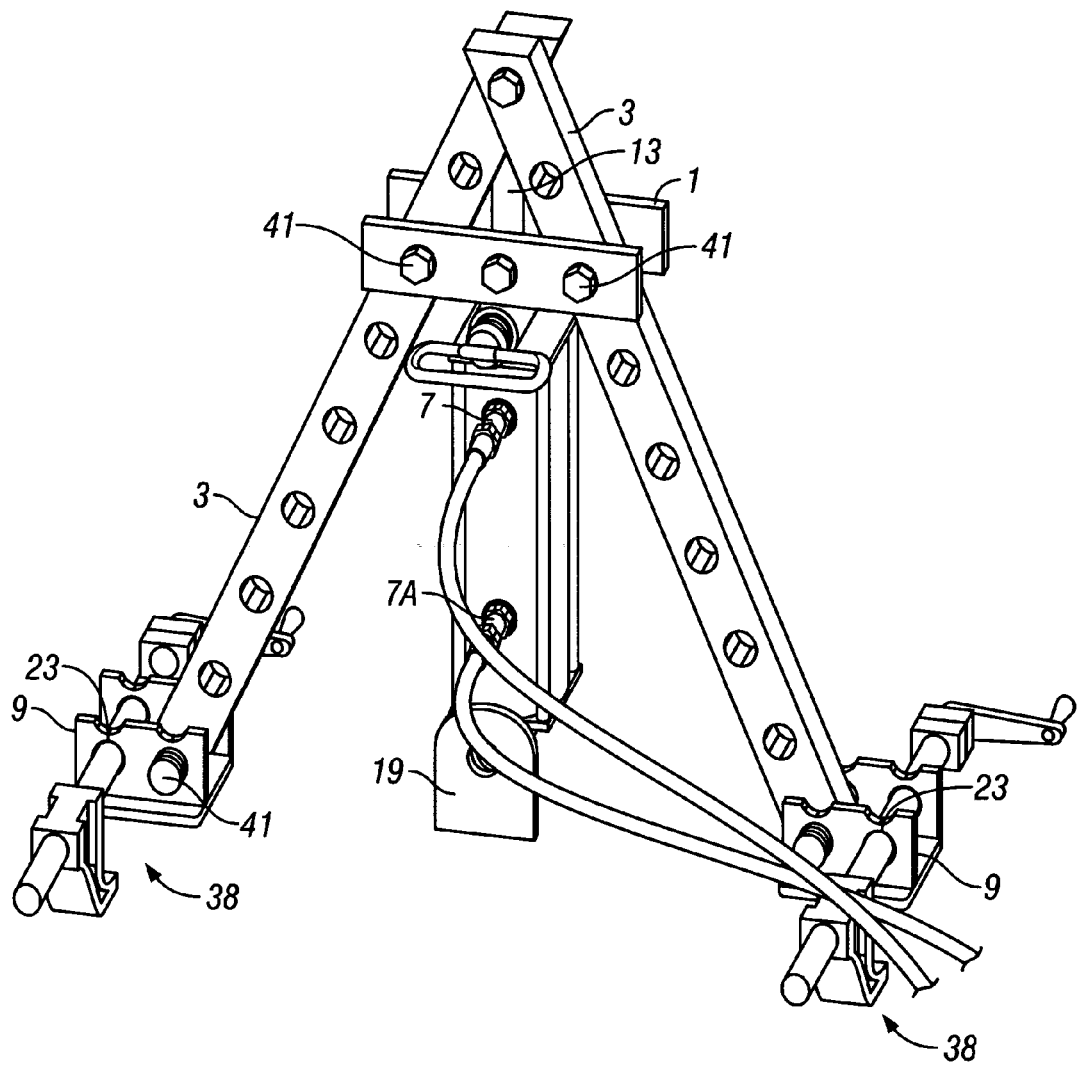
FIG. 8A is another embodiment of FIG. 8 illustrating the option of attachment, of the present apparatus, to the device to be tested, by clamps.

An alternative embodiment of this structure, shown in FIGS. 8 and 8A, could be an A-frame wherein the cylinder is attached to a crossbar or the apex of the A-frame.

Figure 3:
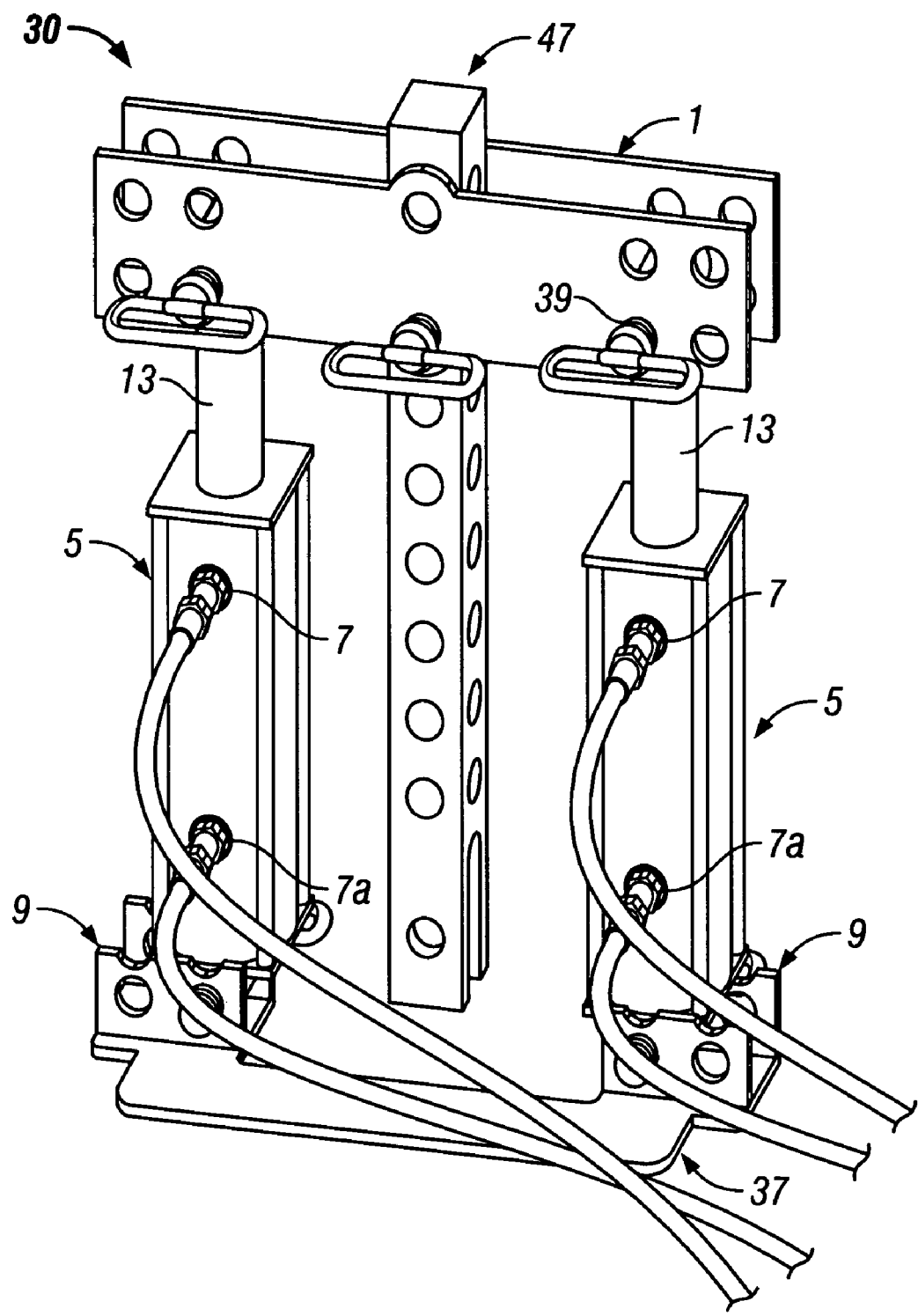
FIG. 3 is a front view assembly drawing of an additional embodiment of the testing apparatus.

FIG. 3 is an assembly drawing of an additional embodiment of the present apparatus.

Figure 4:
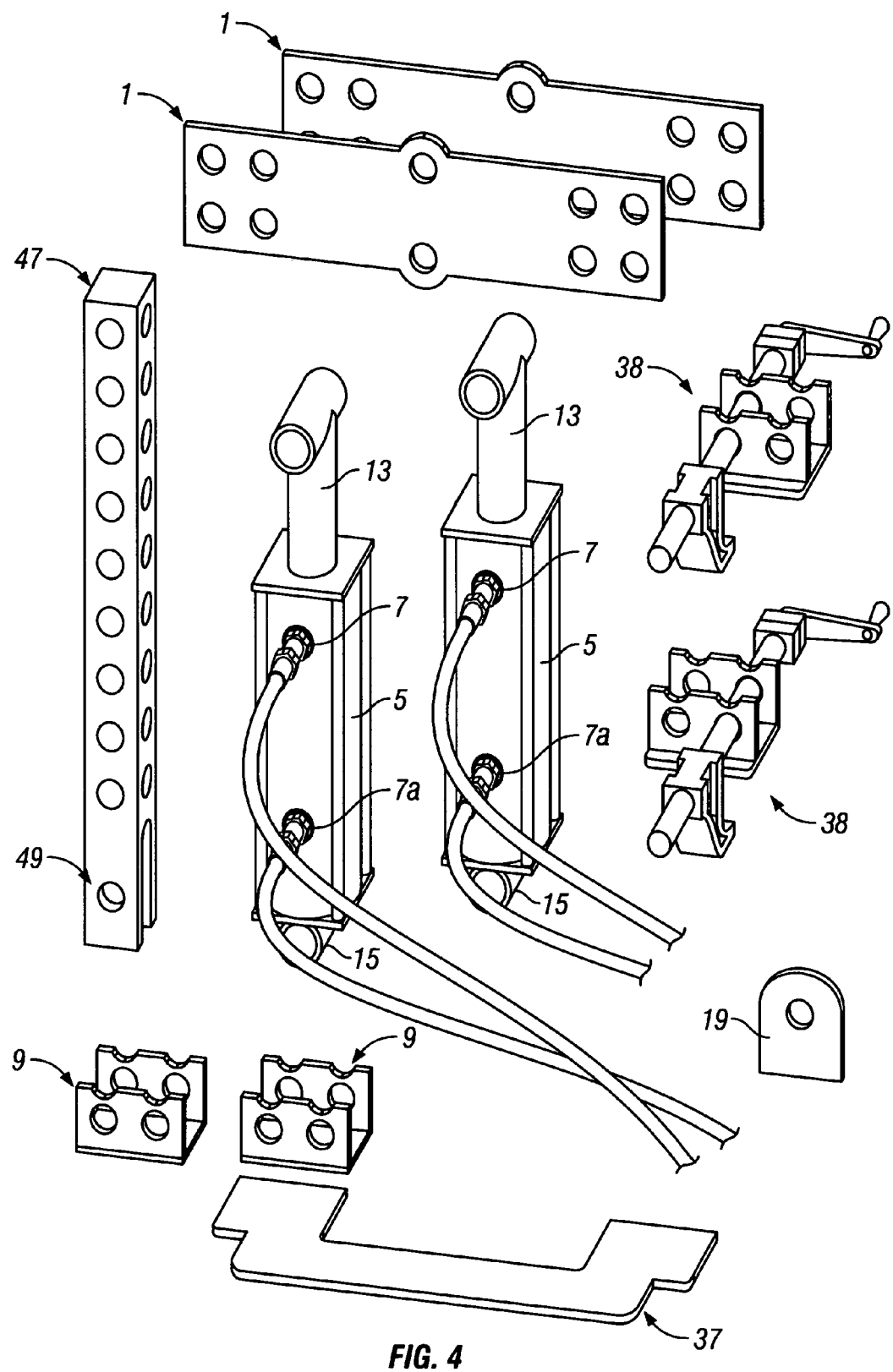
FIG. 4 is a front view of FIG. 3 in its disassembled state.

FIG. 4 shows the individual components of said additional embodiment 30 which is preferably comprised of the two cylinders 5, one being the right side cylinder and one being the left side cylinder, two bridge plates 1, the support beam 47, and two footings 9 comprised of a right side footing and a left side footing.

It should be appreciated that the footings 9 and the attachment plates 17 are an illustrative method of attaching the apparatus to the pad eye 19 or lifting lug. Other ways of attachment which provide adequate support and connection can be employed without departing from the scope thereof. The test apparatus can be mounted to a base plate 37 in order to provide support for the test apparatus, it can be used without the base plate 37 and attached via clamps 38 or other suitable method directly to the base support structure to which the pad eye 19, lifting lug, or other lifting connection is attached.

Figure 3A:
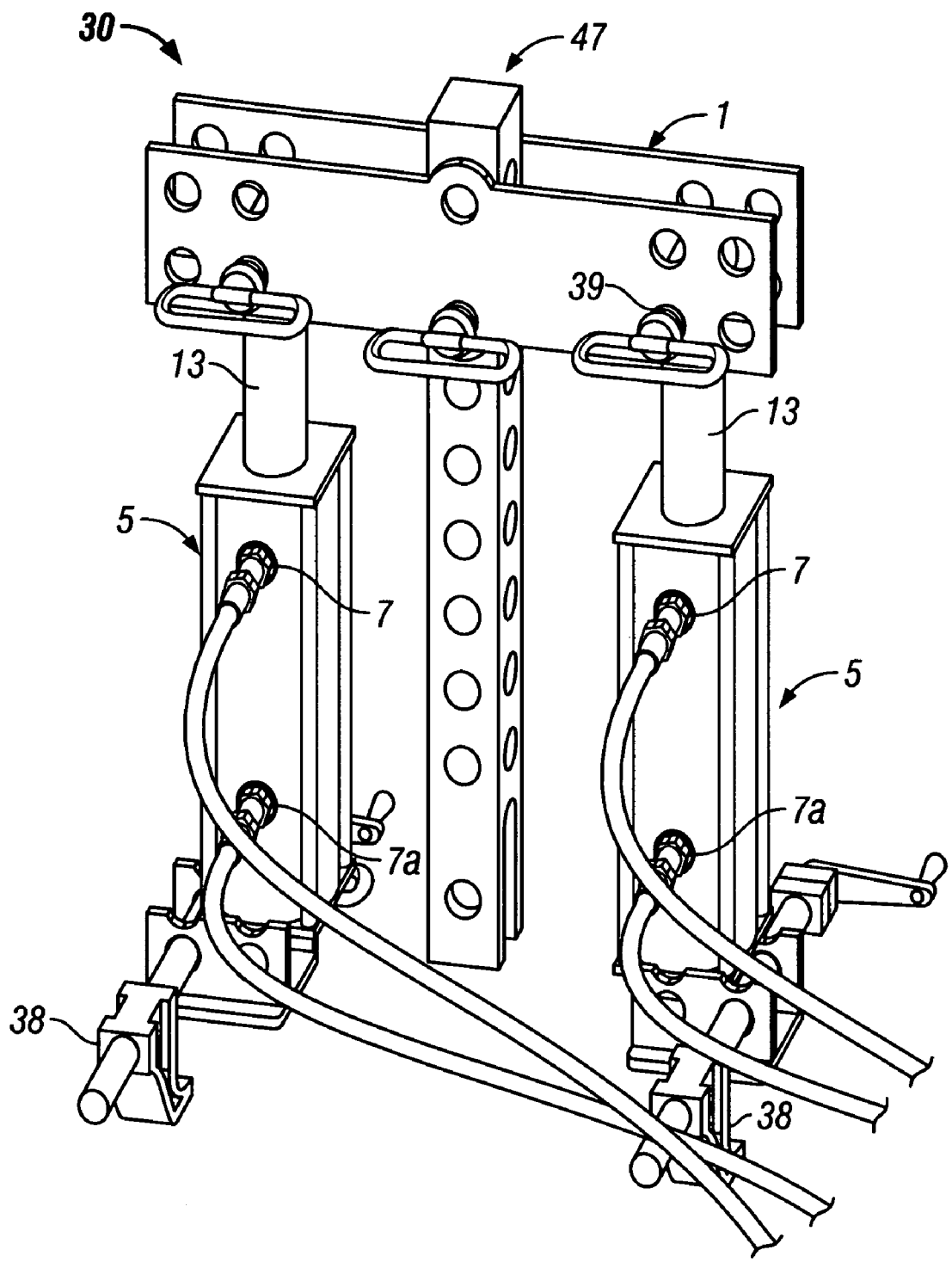
FIG. 3A is another embodiment of FIG. 3 illustrating the option of attachment, of the present apparatus, to the device to be tested, by clamps.

As shown in FIG. 3, FIG. 3A, and FIG. 4, the two cylinders 5 are comprised of similar components as the cylinder 5 for the single cylinder apparatus. It should be appreciated that since the actual cylinder size may change according to the required load the components may also change in size. Both the cylinder shaft 13 and the bottom adaptor 15 are adapted to allow connection to mating parts preferably utilizing a pin connection. The cylinder shaft 13, of the right side cylinder 5 is fixedly attached by a pin 39 to the right end and in between the two bridge plates 1. The cylinder shaft 13, of the left side cylinder 5, is fixedly attached by a pin 39 to the left end and in between the bridge plates 1. The bottom adaptor 15, of the right cylinder 5, is fixedly attached, by a pin 39 to the right side footing 9. The bottom adaptor 15, of the left cylinder 5, is fixedly attached, by a pin 39 to the left side footing 9. It should be noted and appreciated by those in the art that the figures illustratively show two types of pins 39, 41. However, these pins 39, 41 can be interchanged as well as be substituted by a variety of other attachment methods as mentioned above. Both the right side and left side cylinders 5 are each fitted with two cylinder fittings 7 and 7a. For the preferred utilization of the present device, pressure containing hoses are connected to the two cylinder fittings 7 and 7A on each cylinder 5.

Each of the two bridge plates 1 is preferably substantially identical flat rectangular bars made of steel or a material with similar strength properties. These said bridge plates have a plurality of apertures 23 which are used for the fixed connections between the two bridge plates 1 and the cylinder shafts 13, of both cylinders 5, and the support beam 47. It should be appreciated that the hole 23 diameter and consequently the diameter of the pin 39 varies in size depending on the load which will be tested and are typically sized by calculation based on the maximum load contemplated. Preferably, there are a plurality of apertures 23 located on the right and left lengthwise ends of the bridge plate 1 and also located substantially symmetrically around the lengthwise and widthwise centers of the said bridge plates 1. Preferably, the said apertures 23, located on the right and left lengthwise ends, should be substantially symmetrically located at each end of the bridge plates 1. Preferably, said apertures 23, at each end of said bridge plate 1, are substantially symmetrically located with respect to said bridge plate 1 and each other. The said apertures 23 located approximately midway of both the lengthwise and widthwise centers of said bridge plates 1 are preferably substantially symmetrically located at said midway point. The multiple apertures 23 are used for allowing vertical and horizontal adjustment of the test apparatus.

The support beam 47 is preferably a fabricated hollow rectangular beam, having a top side and a bottom side, in which two opposing bottom sides extend, in the lengthwise direction, beyond the other two opposing sides. The said opposing extended sides form a channel at the bottom end of the said support beam 47. The support beam 47 has a plurality of apertures 23 on all four faces of the rectangular beam which are used for the fixed connections between the support beam 47 and the two bridge plates 1 and the two footings 9. It should be appreciated that the hole 23 diameter and consequently the diameter of the pin 39 varies in size depending on the load which will be tested and are typically sized by calculation based on the maximum load contemplated. Preferably, said apertures 23, on each face of the support beam 47 are substantially centered lengthwise on each face of the support beam 47 and are preferably substantially symmetrically spaced from the top of said support beam 47. The multiple apertures 23 are used for allowing vertical and horizontal adjustment of the testing apparatus. As shown in FIG. 4 and described above, the bottom channeled end of the support beam 47 has a hole on each face of the channel portion. These hole diameters are substantially symmetrically located in the center of each face of the said support beam bottom channel. As described above and shown in FIG. 3, the support beam 47 is fixedly attached near the top end of the beam sandwiched between the two bridge plates 1 preferably utilizing the pin 39. The bottom-channeled end of the support beam 47 is set over the pad eye 19. The said bottom channeled end of the support beam 47 is fixedly attached, preferably by pin 39, to the pad eye 19.

The two footings 9 are preferably comprised of a steel, or a material with similar strength properties, channel bar. Preferably, the two channel sides have matching apertures 23 on each face. Preferably said hole diameters are substantially symmetrically centered relative to the said channel bar height and substantially symmetrically spaced between the respective hole centers on each channel wall face. The two footings 9 will preferably be attached by welding to the test apparatus base plate 37 or attached by clamps to the pad eye base plate (not shown). Preferably, the two footings 9 are substantially horizontally and symmetrically centered on each side of the pad eye 19. This said placement, of the two footings 9, is assured through the substantially symmetric connection of the right and left cylinders 5 to the bridge plates 1. This said positioning insures that the testing apparatus will provide an approximately equal upward force on the pad eye 19.

Figure 10:
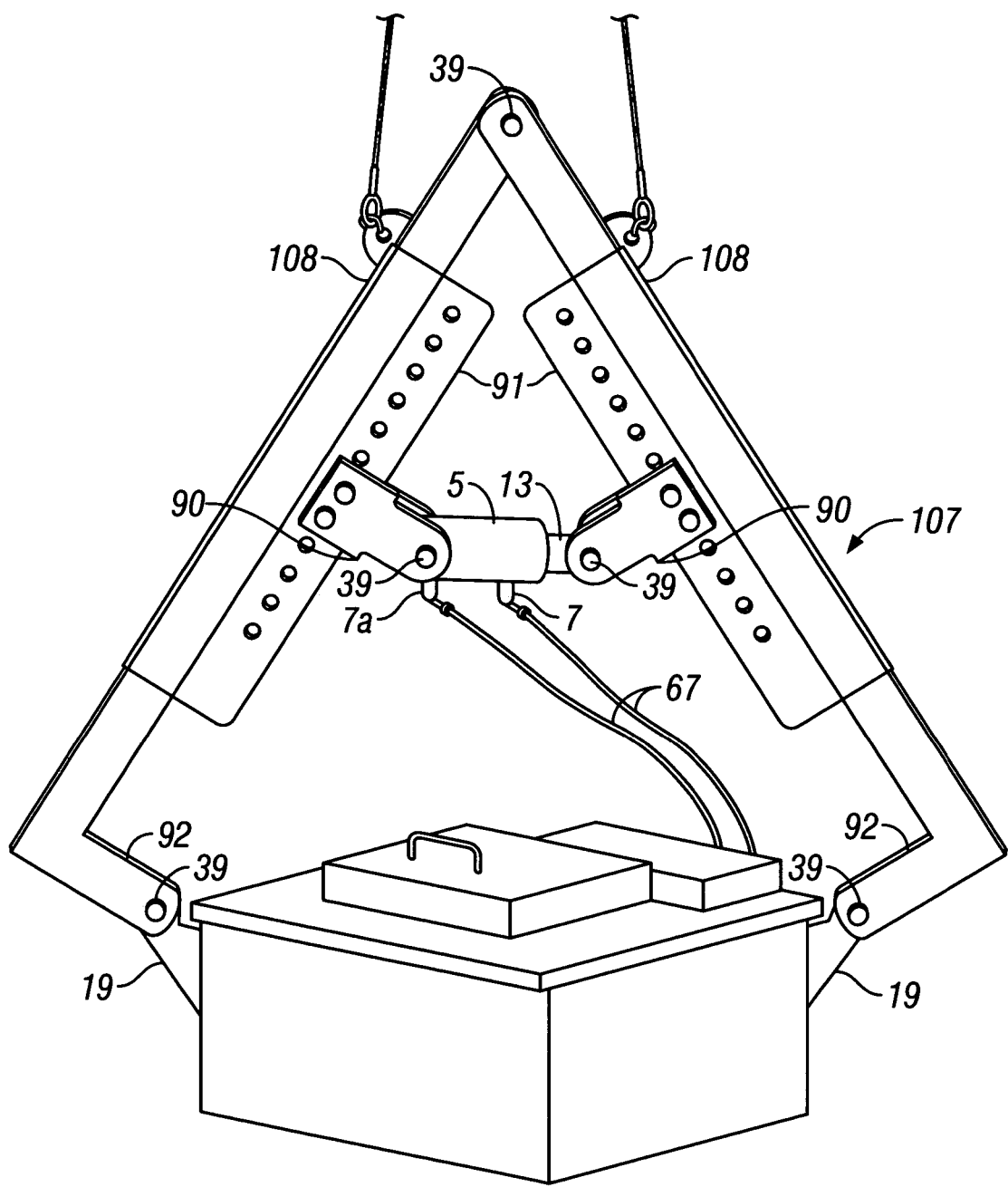
FIGS. 10 and 10A show a front elevation view of a dual load tester of the invention.

FIG. 10 illustrates an alternate embodiment of the invention, a dual load tester 107. Dual load tester 107 permits the simultaneous load testing of two connecting members, such as pad eyes 19 or lifting lugs. Referring to FIG. 10, dual load tester 107 includes opposing arms 108. The first ends 92 of arms 108 are connected by pins 39 to pad eyes 19. The second ends of arms 108 are pivotally connected by pin 39. Brackets 90 are preferably releasably attached to the insides of arms 108 and are adjustable along the lengths or arms 108. A hydraulic cylinder 5 having a retractable and cylinder shaft 13 is mounted between brackets 90. The hydraulic fluid is supplied to cylinder 5 through hoses 67 attached to cylinder fittings 7 and 7a. A hydraulic pump, flow control manifold, and directional valve (not here illustrated) may be used to increase the hydraulic pressure on, and to move a piston in, cylinder 94 so as to urge arms 108 apart.

Figure 10A:
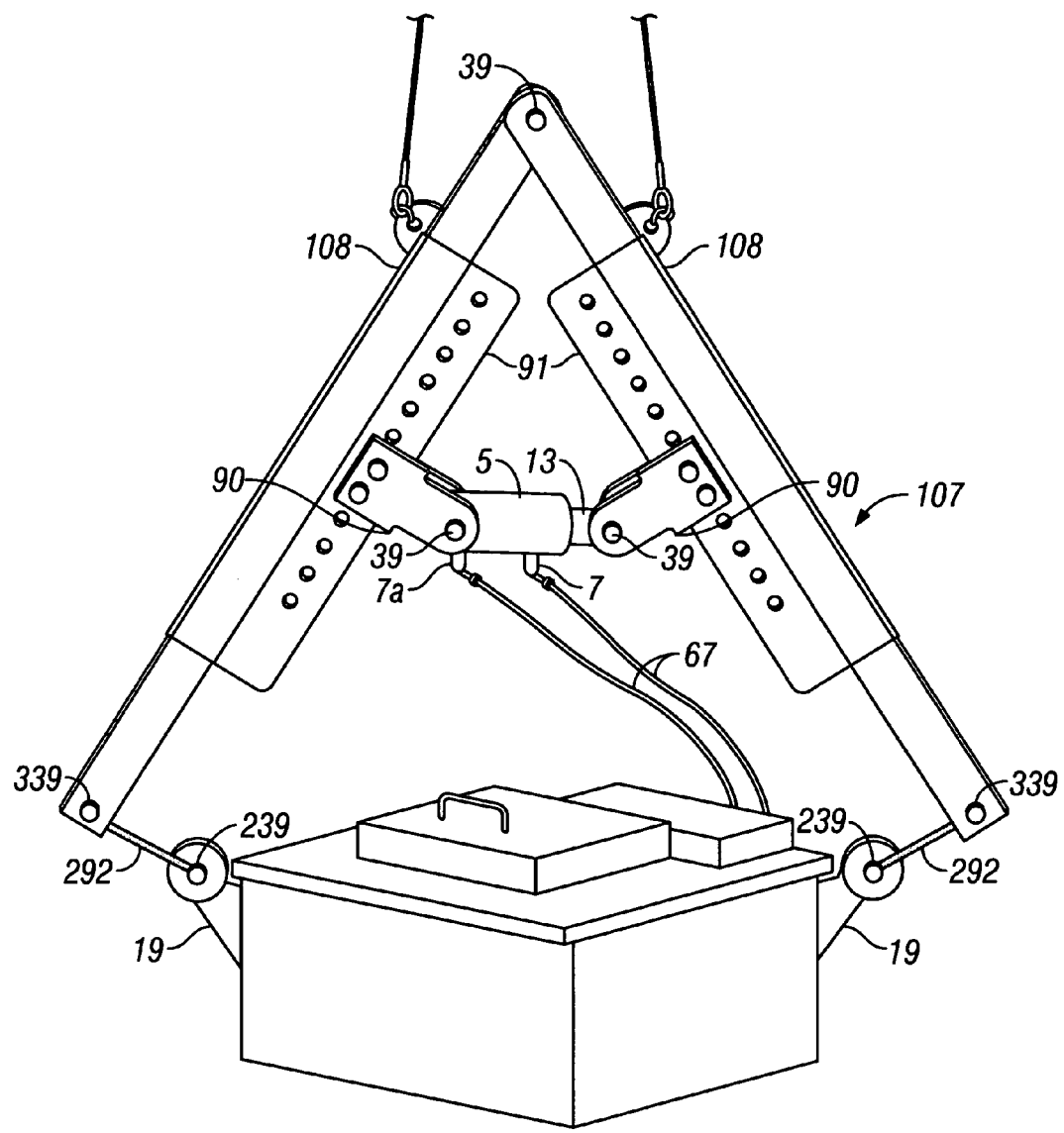

FIG. 10a is substantially similar to FIG. 10 except that the first end of arms 108 is attached to the pad eye 19 by the use of a tension cable 292, which can be but is not limited to a steel or other high tensile strength cable. Tension cable 292 can be attached to arm 108 via a pin 339 through an O-loop arrangement of cable, or any other means conventional in the art. It should be noted that cable 292 can be a plurality of cables. Tension cable 292 can be attached to pad eye 19 via a pin 239 through an O-loop arrangement of cable, or any other means conventional in the art.

It should be appreciated that one skilled in the art would recognize that the pistons utilized in all embodiments of this invention could be attached to the pad eye, lug, or test piece via the use of alternate attachment means, such as but not limited to, cables or tension wires. It should also be appreciated that one skilled in the art would recognize that cables or tension wires could be utilized in attaching pistons to a variety of frameworks including, but not limited to, support columns, bridge plates, cross bars, mounted framework, arms, brackets, or footing. It should also be appreciated that one skilled in the art would recognize that cables or tension wires could be utilized in attaching the test piece to a variety of frameworks or bridges including, but not limited to, support columns, bridge plates, cross bars, mounted framework, arms, brackets, or footing.

Figure 11:
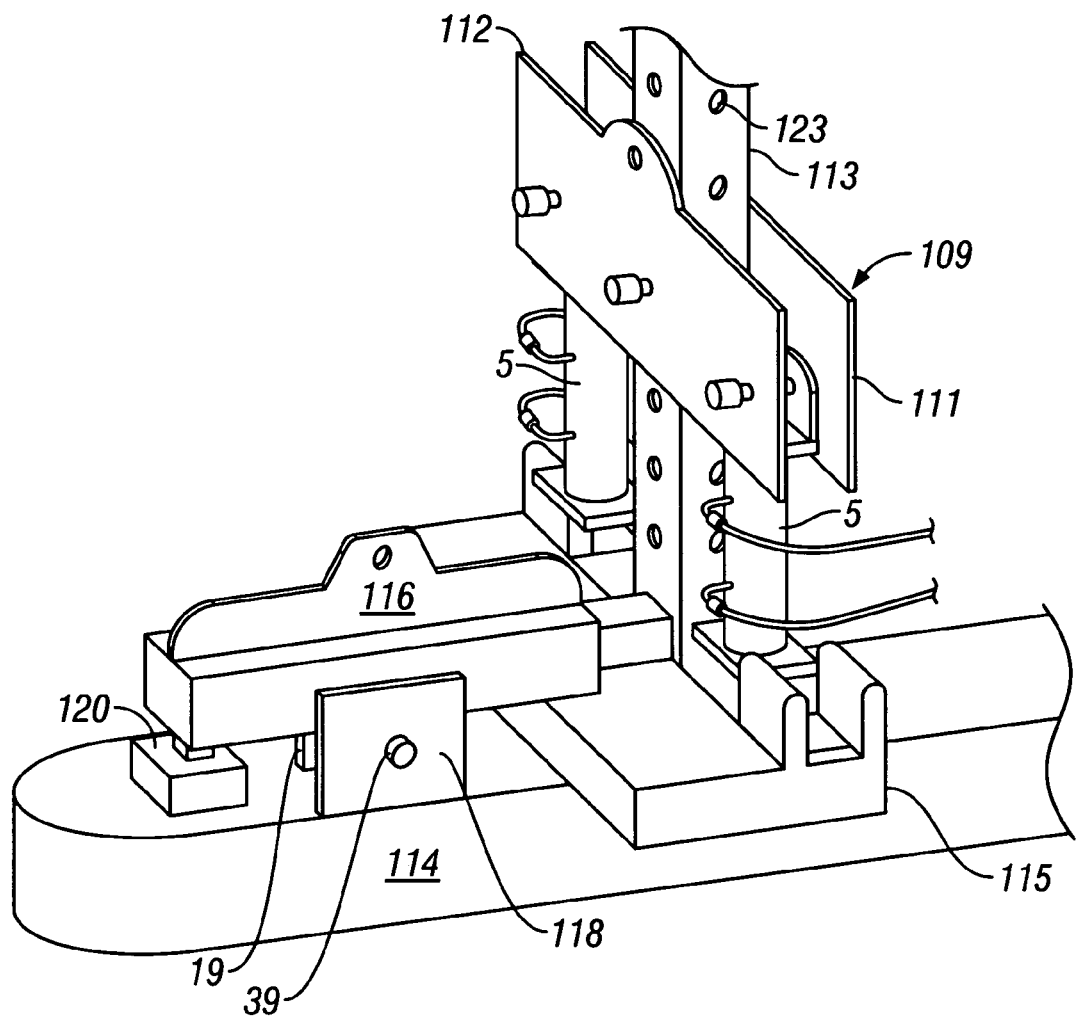
FIG. 11 is a perspective view of a bar load tester of the invention.

FIG. 11 illustrates an alternative embodiment of the invention, a bar load tester 109. Bar load tester 109 permits load testing of a pad eye 19 or lifting lug mounted on a bar 114. Frame 111 of bar load tester 109 includes a base 115, bridge plates 112, and a support column 113. Support column 113 has a spaced apart plurality of apertures 123. Base 115 is preferably immovably supported by bar 114. Hydraulic cylinders 5 preferably have lower ends releasably attached to base 115 and cylinder shafts 13 on their upper ends being releasably attached to bridge plates 112. As hydraulic fluid pressure in cylinders 5 increases, their shafts extend so as to move bridge plates 112 and support column 113 upward and away from base 115, as previously described with respect to the foregoing described embodiments of the invention. A lever arm 116 is substantially supported on one end preferably by support column 113. Flange 118 on lever arm 116 is temporarily pinned to pad eye 19 on bar 114. Post 120 supported by bar 114 provides additional support to lever arm 116 when needed.

Figure 12:
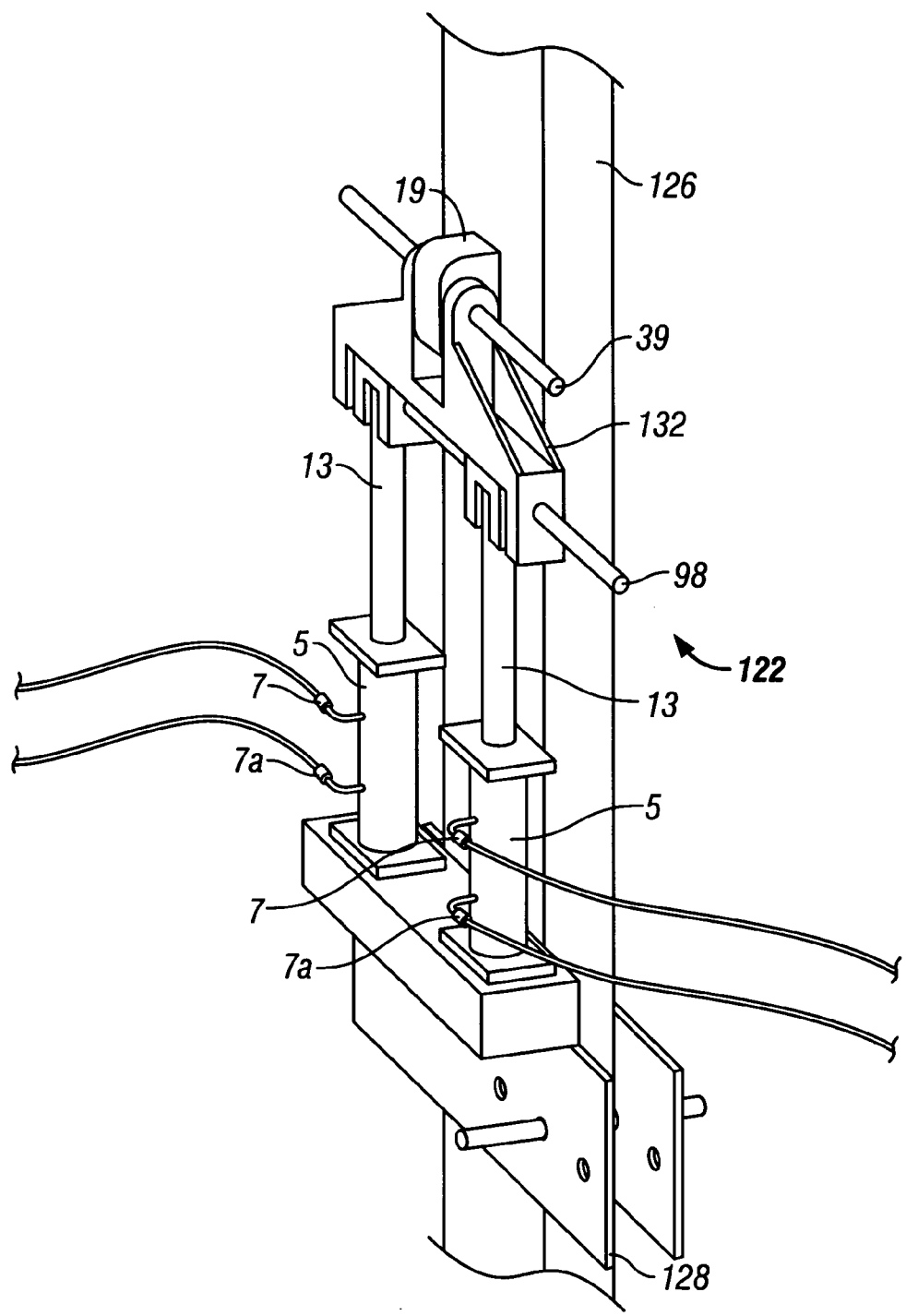
FIG. 12 is a perspective view of a beam load tester of the invention.

FIG. 12 illustrates an alternative embodiment of the invention, a beam load tester 122. Beam load tester 122 permits load testing of a pad eye 19 or lifting lug installed on a beam 126. Base 128 of beam load tester 122 is clamped to beam 126 and supports the lower ends of hydraulic cylinders 5 in a conventional fashion. The cylinder shafts 13 are connected at their upper ends to bracket 132 by preferably a bar pin 98. Bracket 132 is also temporarily pinned to pad eye 19 by a pin 39.

Figure 13:
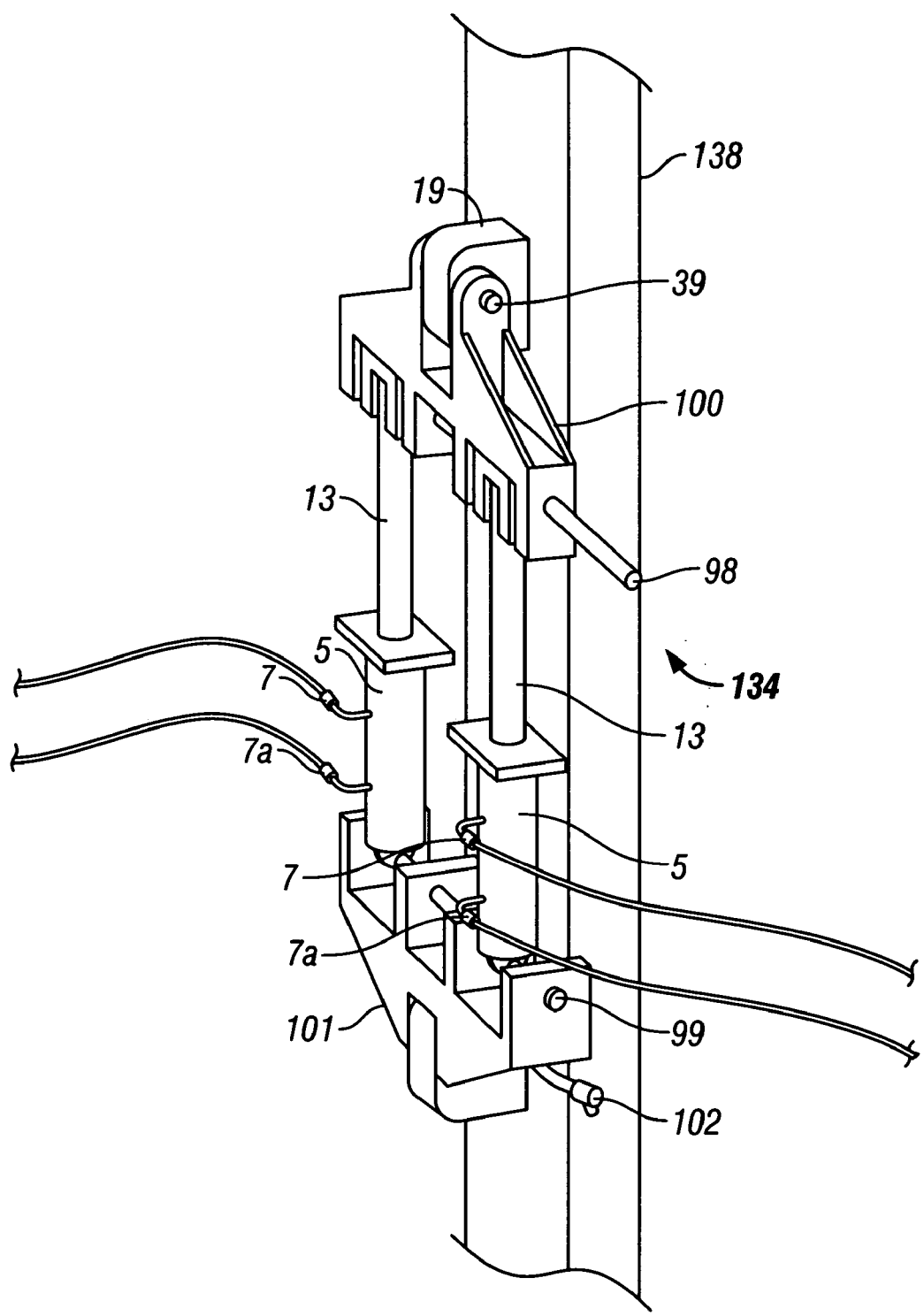
FIG. 13 is a perspective view of a post load tester of the invention.

FIG. 13 illustrates an alternative embodiment of the invention, a post load tester 134. Post load tester 134 advantageously permits load testing of a pad eye 19 or lifting lug installed on a post 138. Base 101 of load tester 134 is attached to post 138 by, but is not limited to, clamps 102 and supports the lower ends of hydraulic cylinders 5. Lower end of cylinders 5 is attached to base 101 by, but is not limited to, pin 99. The shafts 13 of cylinders 5 are connected at their upper ends to bracket 100 by, but not limited to, pins 98. Bracket 100 is also temporarily pinned 39 to pad eye 19.

Figure 14:
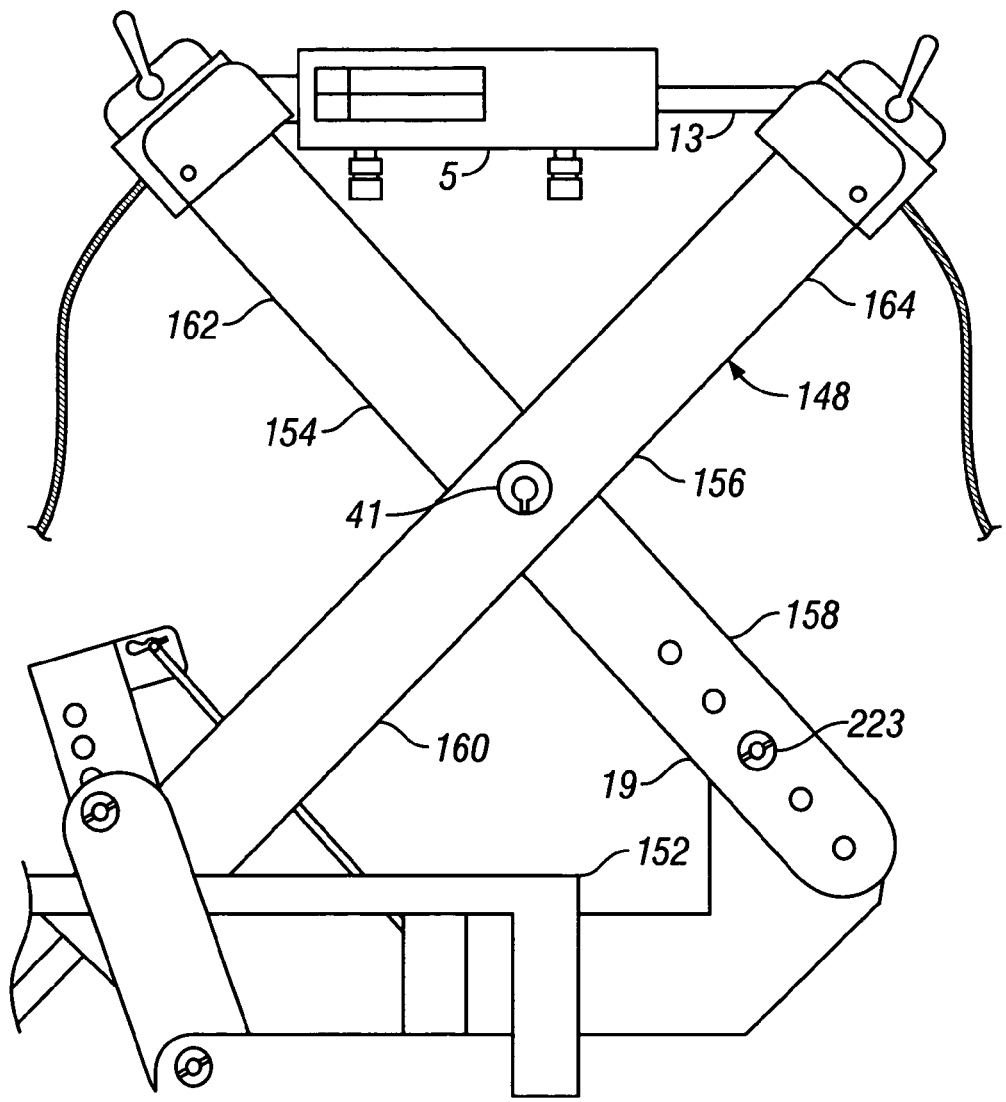
FIG. 14 is a front elevation view of a basket load tester of the invention.

FIG. 14 illustrates an alternative embodiment of the invention, a basket load tester 148. Basket load tester 148 permits load testing of a pad eye 19 or lifting lug installed on a basket or beam 152. Load tester 148 includes opposing arms 154 and 156 pivotally connected near their centers by pin 41. The connection at pin 41 permits rotational movement between arms 154 and 156 in scissor-like fashion. The connection pin 41 holds the arms 154 and 156 in substantially an "X" formation. Lower end 158 of arm 156 has a spaced apart plurality of apertures 223 and is temporarily pinned to a pad eye 19 or lift lug on basket or beam 152. Lower end 160 of arm 154 is temporarily anchored to basket or beam 152. The upper ends 162 and 164 of arms 154 and 156, respectfully, are releasably connected by hydraulic cylinder 5 and shaft of cylinder 13 in a conventional manner.

It should be understood that the frames in these embodiments could be modified in many aspects to achieve the substantially same function and substantially same result of the present device. For instance, the bridge plate 1 could be curved, angled, have additional members attached thereto, and the like. The structure and frame could be further modified using springs or other mechanisms to exert a tensioning force on the pad eye or lifting lug attachment weld.

Operating Apparatus

Figure 5:
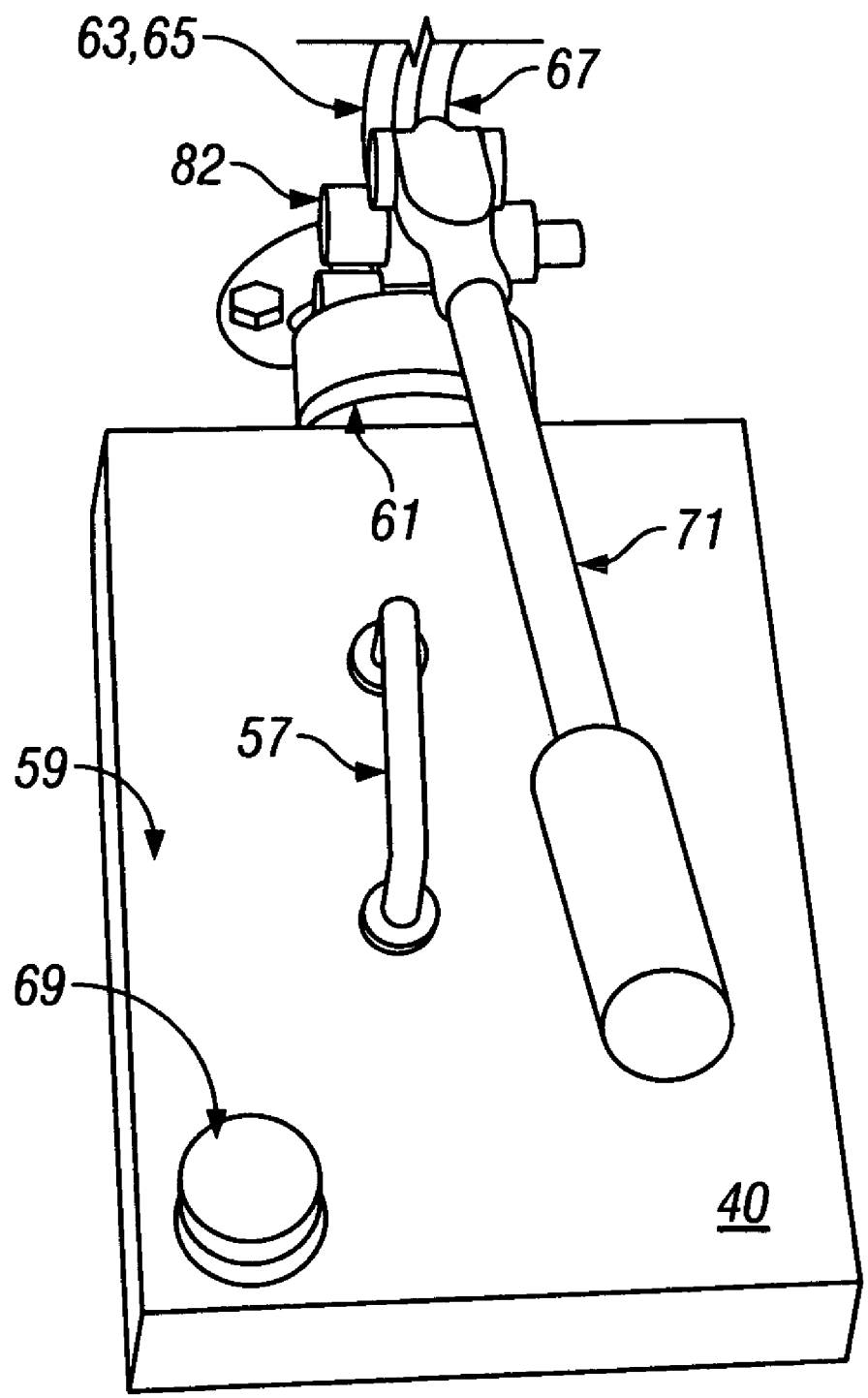
FIG. 5 is a pictorial view of the hand pump.

Preferably, as shown in FIG. 5, the hand pump 40 is basically comprised of a reservoir 59, a carrying handle 57, a pump 61, the pumping handle 71, a pump inlet 65, a pump outlet 63, fittings 82, hoses 67 and a reservoir cap 69. It should be appreciated that although FIG. 5 shows a small typical hand pump, many varieties and combinations of pumps and fluid reservoirs or accumulators could be used to actuate this test apparatus. For the present device, a small hand pump is well suited for portability. If an adaptation of this apparatus were, for example, to be used in an industrial setting the pump may be otherwise powered, may be stationary, have larger reservoirs, use accumulators, use different fluids, or a multitude of different adaptations. For the present contemplated usage of this device, the cylinder shaft 13 is preferably actuated by a hand pump 40. The hand pump 40 is connected to the flow control manifold 50 (FIG. 6) by pressure containing hoses. The pump 61 is operated through the use of the pump handle 71.

Figure 6:
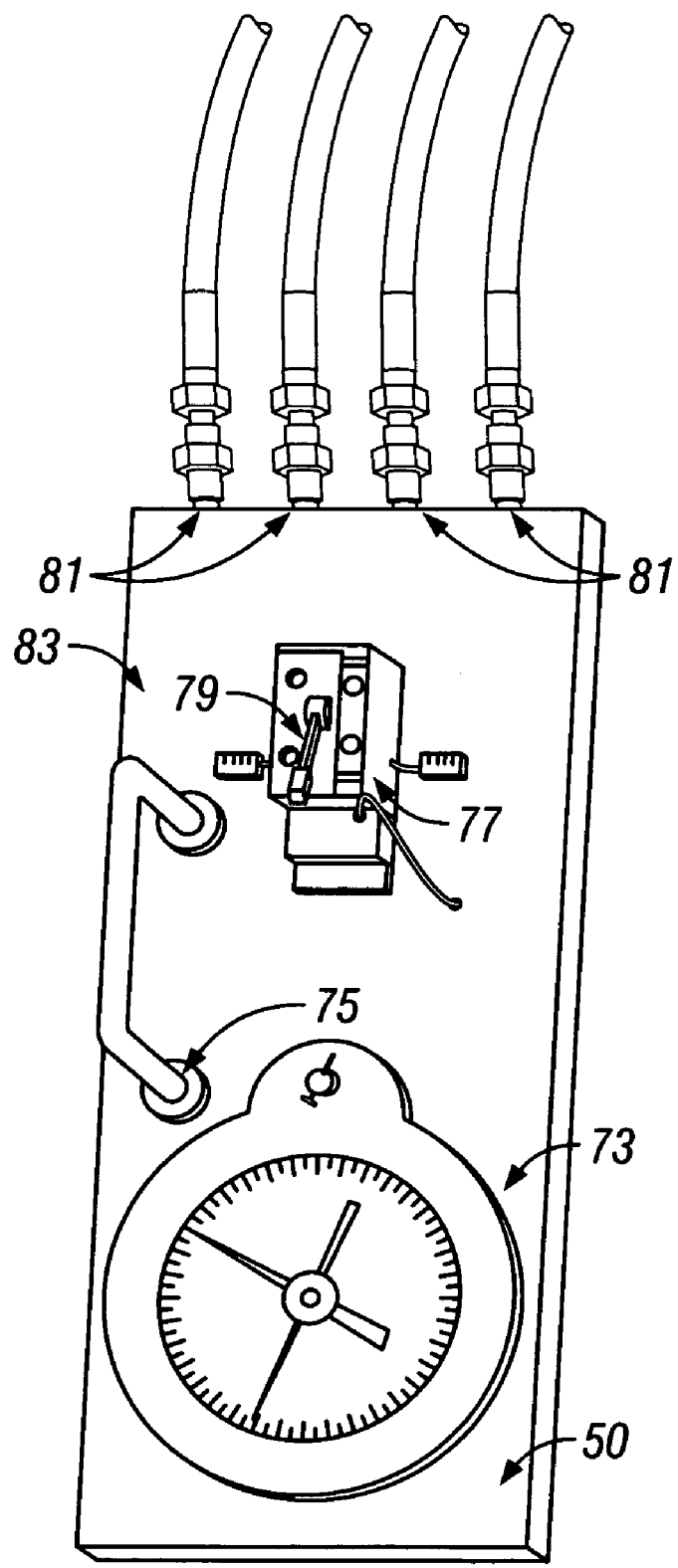
FIG. 6 is a pictorial view of the flow control manifold.

As shown in FIG. 6, the flow control manifold 50 is comprised of a manifold 83, fittings 81, a pressure gauge 73, a directional valve 77, a directional lever 79, and a carrying handle 75. The direction of actuation and flow is preferably controlled by a directional valve 77. The directional valve 77 is further controlled by the rotational directional lever 79. Preferably the said directional lever can only be turned approximately ninety degrees in one direction and then approximately ninety degrees in the opposite direction. It should be appreciated, as with the hand pump above, that this is a typical manifold selected for the presently contemplated use of this device. However, as this apparatus is adapted for any variety of locations, the type, size, and configuration of the flow control manifold, including the type and configuration of the directional valve 77, as well as even the method of flow control itself may require substantial change. The flow control manifold 50 is preferably connected to the upper 7 and lower 7A cylinder fittings by means of pressure containing hoses 67. The flow control manifold 50 controls the direction of flow either into the lower cylinder fitting 7A, causing the cylinder shaft 13 to extend, or into the upper cylinder fitting 7 causing the cylinder shaft 13 to retract. The flow control manifold 50 also measures the pressure of the fluid. This pressure is shown on the mounted gauge but is also available to be displayed on a variety of recorders, computers, controllers, and the like.

In use, the present device can be transported in the disassembled condition to any location where some pad eye or lifting lug will be utilized or requires testing. One possible criterion for selecting a particular embodiment may be the required test load.

In use, prior to selecting the proper embodiment of the present device, the desired test load must be known. Typically, this value will be approximately 1.5 times greater than the rated load capacity of the pad eye or lifting lug. If such a rated load is not readily accessible, the test value would be approximately 1.5 times the weight that will be supported by the pad eye or lifting lug. It should be understood that the said multiplying factor of 1.5 is only a preferred safety factor; therefore, the value can vary depending on a user's experience or preference and should not be used as a limiting factor of the scope of the claimed apparatus. After determining the said load test value, the proper testing apparatus will be comprised of the correct size and number of cylinders 5 which can generate the required test load. The required test load is generated by the cylinder 5 and is produced by the combination of the pressure, produced by the hand pump 40 and measured by the manifold pressure gauge 73, acting over the effective area of the cylinder. The effective area of the cylinder is calculated based on the diameter of the piston 53 within the cylinder 5. As is known to those in the art, the effective area of the piston 53 can be obtained from the cylinder manufacturer. As is also well known to those in the art, the said effective area is multiplied by the pressure to predetermine the produced test load. After determining the test load as described above, selecting the cylinder size, as described above, and determining the required pressure to produce the said test load, as described above, the hand pump 40 is used to produce the required pressure.

In use, the test apparatus is assembled as shown in FIGS. 1, 1A, 3, or 3A and discussed above. The apparatus is then connected to the pad eye 19, lifting lug, or other device to be tested. The connection, as shown in FIGS. 1 and 1A can include the use of attachment plates 17. In addition, a pressure containing hose 67 is connected to each of the cylinder fittings 7 and 7A on the cylinders 5. The other end of each pressure containing hose is connected to the flow control manifold 50. The preferred embodiment utilizes "quick connect" connectors for the pressure containing fittings, however, other types of pressure containing fittings may be utilized. Preferably, the cylinder fittings 7 and 7A, the manifold fittings 81, and the pump fittings are all male "quick connect" pressure containing fittings. Each pressure containing hose is preferably comprised of some length of hydraulic quality hose with a female "quick connect" fitting on each end. The pressure containing hose will have a pressure rating which exceeds the pressure required for the testing. Another set of the above described pressure containing hoses is connected between the flow control manifold 50 and the hand pump 40. It should be understood that the exact sequence and location of connection of the pressure containing hoses may vary depending on the version of the testing apparatus as well as the type and model of pump and flow control manifold. After the pressure containing hoses have been connected, the pressurized system, comprised of the hoses and associated fittings, the hand pump 40, the flow control manifold 50, and the cylinders 5, is known to those in the art as a closed system. Therefore, any air, contained in the closed pressurized system must be removed. The said air removal is known as system bleeding to those in the art. The preferred method of bleeding the system is by moving the pressurized fluid through the pressurized system, which forces any air through the system and into the reservoir. After this is performed, the entire system is filled only with the pressurized fluid. The movement of the fluid is accomplished by alternately moving the pump handle 71 in an upwardly and downwardly motion. This said movement of the pump handle 71 causes the pump to push fluid through one of the hoses, through the flow control manifold 50, and into the lower cylinder fitting 7A. This causes the said fluid to flow underneath the piston 53 and begin forcing the piston 53 in an upwardly direction. As the piston 53 begins to rise, the fluid, resting above the piston 53 begins to be forced out of the upper cylinder fitting 7, through the pressure containing hose, connected to the upper cylinder fitting 7, through the flow control manifold 50, through the pump 61, and into the reservoir 59. This described flow and the accompanied rise of the piston 53 causes the cylinder shaft 13 to extend.

Turning the directional lever 79 ninety degrees from the position described in the above paragraph will cause the fluid to flow into the upper cylinder fitting 7 when the pump 61 is actuated by the moving the pump handle 71 in alternating upwardly and downwardly directions as described above. The said pump handle 71 movement causes the pump to push fluid through one of the hoses, through the flow control manifold 50, and into the upper cylinder fitting 7. This causes the said fluid to flow above the piston 53 and begin forcing the piston 53 in a downwardly direction. As the piston 53 begins to move in the said downward direction, the fluid, resting below the piston 53 begins to be forced out of the lower cylinder fitting 7A, through the pressure containing hose connected to the lower cylinder fitting 7A, through the flow control manifold 50, through the hand pump 40, and into the reservoir 59. This described flow of the fluid and the accompanied downward movement of the piston 53 causes the cylinder shaft 13 to retract.

In use, the single cylinder version of the present device produces an upward force on the pad eye or lifting lug when the cylinder shaft 13 retracts. Therefore, the directional lever 79 shall be moved into the position which causes the fluid to flow into the upper cylinder fitting 7.

In use, the double cylinder version of the present device produces an upward force on the pad eye or lifting lug when the cylinder shaft 13 extends. Therefore, the directional lever 79 shall be moved into the position which causes the fluid to flow into the lower cylinder fitting 7A.

In use, the pressure gauge 73 will indicate the system pressure. As the pump handle 71 is moved, as described above, the pressure, indicated on the pressure gauge will increase. When the indicated pressure is approximately the same as the calculated pressure corresponding to the required test load, as described above, then the proper test load has been applied. It should be understood that this paragraph describes the operation regardless of the direction of fluid flow or the position of the directional valve handle 79.

In use, after the test is completed, the directional valve 79 should be turned ninety degrees, and the pump 61 should be actuated by the pump handle 71, as previously described, until the system pressure, as indicated by the gauge or other monitoring device, is completely relieved.

It should be appreciated that the directional lever 79 does not actually control flow but rather moves the directional valve 77 into a position that changes the flow direction. The detailed workings of the directional valve 77 are well known to those skilled in the art.

Figure 9:
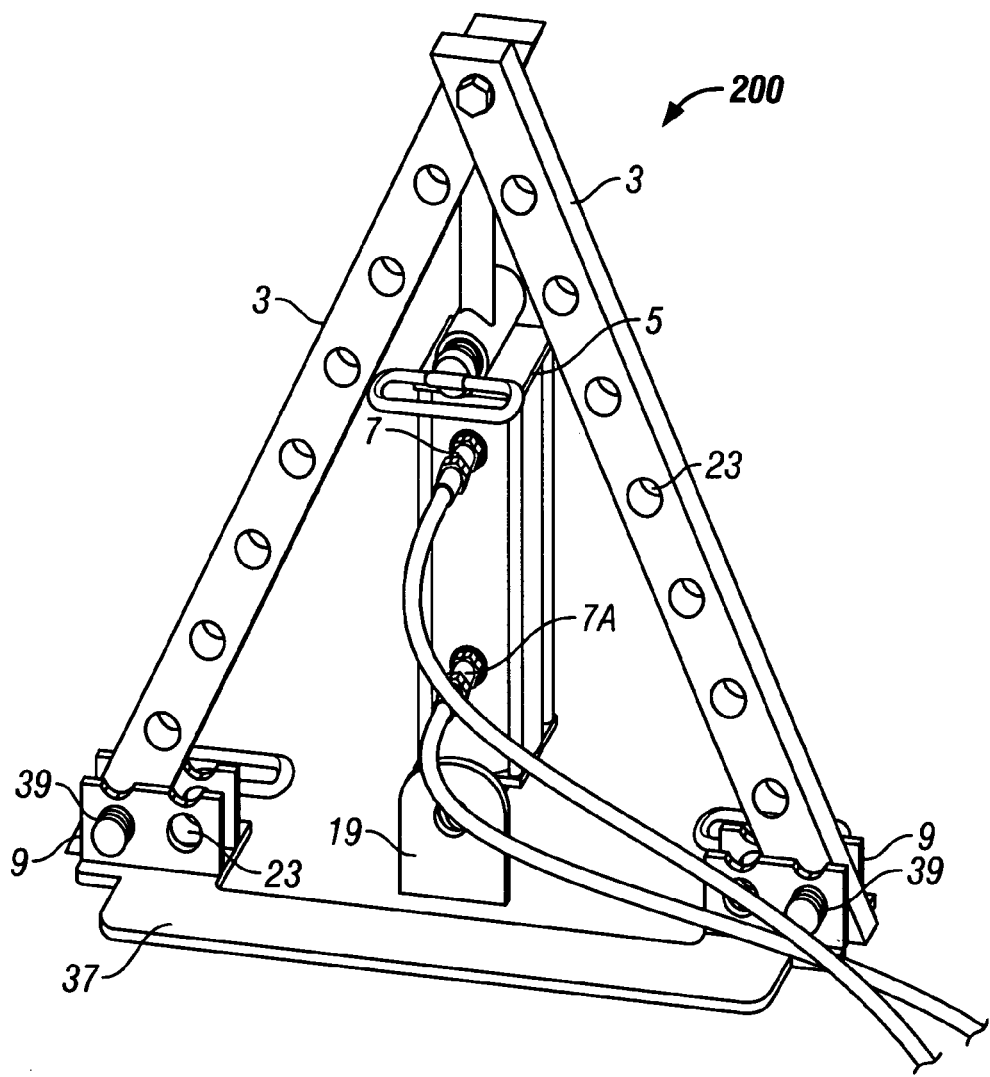
FIG. 9 is a front view assembly drawing of another alternative embodiment of the testing apparatus.
Figure 9A:
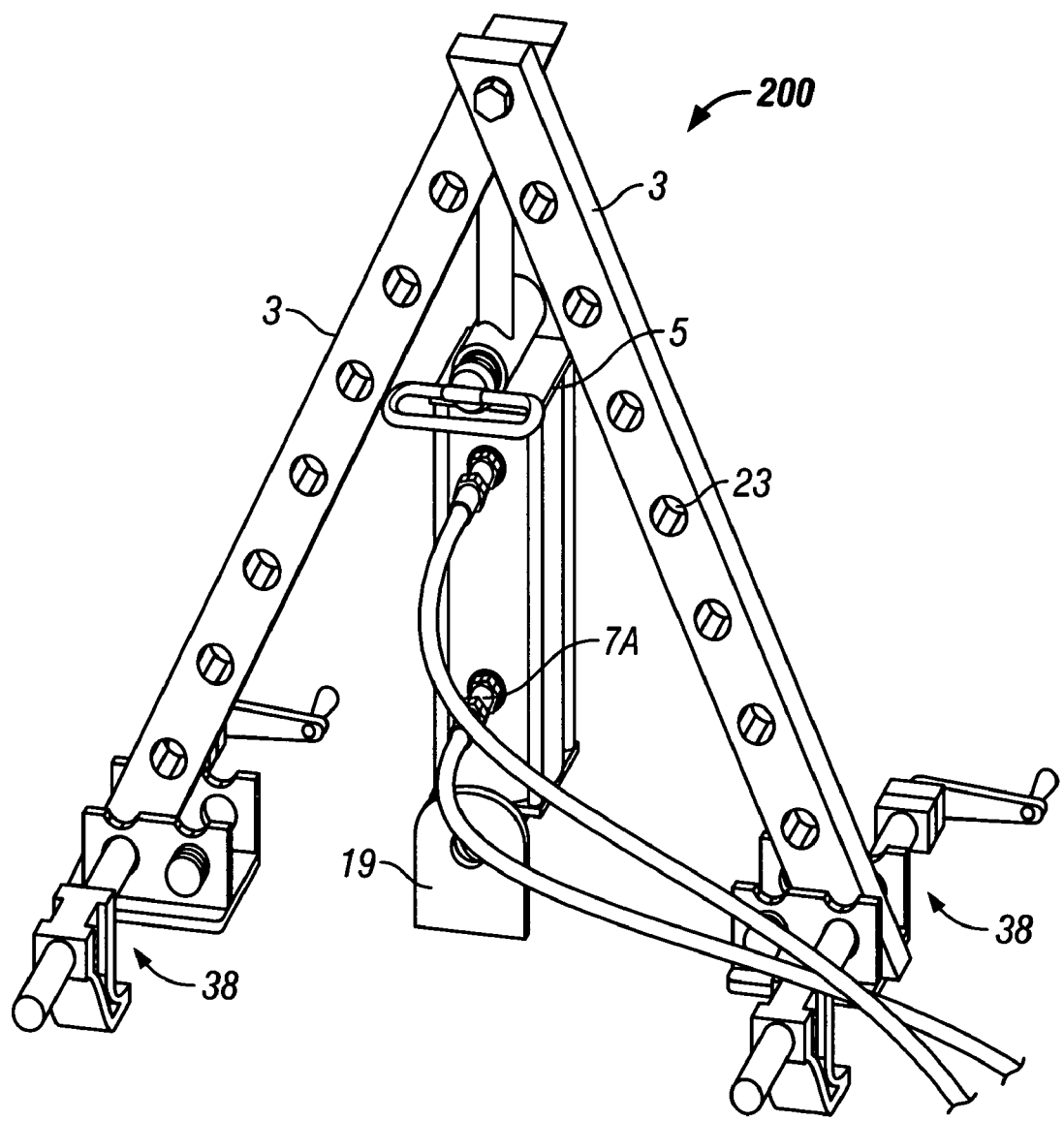
FIG. 9A is another embodiment of FIG. 9 illustrating the option of attachment, of the present apparatus, to the device to be tested, by clamps.

Those who are skilled in the art will readily perceive how to modify the present apparatus still further. For example, most of the illustrated connections utilize pins, however, it should be recognized that other methods of connection may be utilized, such as threaded connectors or if the unit will be modified for permanent installation as opposed to portable, the connections could be welded. Further, the frames or structures, of this apparatus, do not need to be comprised of substantially vertical and horizontal members. These members could be curved, angled, or joined in a manner to provide the substantially same function and substantially same result in testing the pad eye or other lifting lug attachment welds. FIGS. 8 and 9 illustrate two such modifications where the alternative embodiment consists of an A-frame structure and FIG. 8 illustrates a bridge plate or cross bar being used with the A-frame. FIGS. 8A and 9A show an alternative embodiment using clamps 38 for attachment to the base support structure to which the pad eye 19, the lifting lug, or other lifting connection it is attached to. Additionally, there are other means of providing pressure to actuate the cylinders, other configurations for the pump equipment and associated hoses, as well as additional measuring and measurement recording devices which can all be used within and in conjunction with the present device. Further, other pressurized fluids can be used to actuate the cylinders. In addition, the subject matter of the present device would not be considered limited to a particular material of construction. Therefore, many materials of construction are contemplated by the present apparatus including but not limited to various metals or combinations of metals. As many possible embodiments may be made of the present apparatus without departing from the scope thereof, it is to be understood that all matter herein set forth or shown in the accompanying drawings is to be interpreted as illustrative and not in a limiting sense.

FIG. 10 illustrates how dual load tester 107 is used to simultaneously load test two pad eyes 19, the lifting lug, or other lifting connection it is attached to. First ends 92 of arms 109 are attached to the pad eyes 19, the lifting lug, or other lifting connection it is attached to. Hydraulic pressure in cylinder 5 is then increased to extend its shaft, thus urging arms 108 apart and applying tension force to the pad eyes 19, the lifting lug, or other lifting connection it is attached to. A pressure gauge on the flow control manifold (not here shown) is used to monitor the hydraulic pressure as it is increased. The force applied to pad eyes 19, the lifting lug, or other lifting connection it is attached to by arms 108 is readily calculated by the use of pressure gauge 73.

In FIG. 11, the strength and integrity of pad eye 19, the lifting lug, or other lifting connection it is attached to is tested by bar load tester 109 as follows. Cylinders 5 are hydraulically actuated to urge bridge plates 112 and support column 113 away from beam 114. Lever arm 116 is thus urged upward by support column 113, applying a tension force to pad eye 19, the lifting lug, or other lifting connection it is attached to through flange 118. The force applied to pad eyes 19, the lifting lug, or other lifting connection it is attached to by lever arm 116 is readily calculated by the use of pressure gauge 73.

In FIG. 12, the strength and integrity of pad eye 19, the lifting lug, or other lifting connection it is attached to is tested by beam load tester 122 as follows. Cylinders 5 are hydraulically actuated by application of hydraulic fluid fed into cylinders 5 by connections 7 and 7a as needed to extend their shafts 13 so as to urge bracket 132 upward, applying a shearing force to the weld connection between pad eye 19 the lifting lug, or other lifting connection it is attached to and beam 126. The force applied to pad eyes 19, the lifting lugs, or other lifting connection it is attached to by bracket 132 is readily calculated by the use of pressure gauge 73.

In FIG. 13, the strength and integrity of pad eye 19 the lifting lug, or other lifting connection it is attached to are tested by post load tester 134 as follows. Cylinders 5 are hydraulically actuated to extend their shafts so as to urge bracket 100 upward, applying a shearing force to the weld connection between pad eye 19 the lifting lug, or other lifting connection it is attached to and post 138. The force applied to pad eyes 19 the lifting lugs, or other lifting connection it is attached to by bracket 100 is readily calculated by the use of pressure gauge 73.

In FIG. 14, the strength and integrity of pad eye 19 or lifting lug is tested by basket load tester 148 as follows. Cylinder 5 is hydraulically actuated to extend its shaft 13 so as to urge apart the upper ends 162 and 164, and the lower ends 158 and 160, of arms 154 and 156, respectfully. This action applies a tension force to pad eye 19 or lifting lugs through lower end 158 of arm 154. The force applied to pad eye 19 the lifting lugs, or other lifting connection it is attached to by arm 154 is readily calculated by the use of pressure gauge 73.

It may be seen from the preceding description that a new and improved pad eye testing apparatus and method has been provided. Although very specific examples have been described and disclosed, the invention of the instant application is considered to comprise and is intended to comprise any equivalent structure and may be constructed in many different ways to function and operate in the general manner as explained hereinbefore. Accordingly, it is noted that the embodiment of the new and improved pad eye testing apparatus and method described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An apparatus for non-destructively testing the weld strength and integrity of at least one weld when desired comprising:

a framework including at least two pieces;

at least one fluid containing cylinder, for moving a piston therein inwardly and outwardly as fluid is moved out of or into the cylinder, respectively;

an attachment structure for attaching to a pad eye or any device to be tested;

a base;

said base including a clamp;

said at least one fluid containing cylinder attached to said clamp;

at least one bracket; and said at least one bracket being releasably attached to said pad eye;

whereby moving fluid into said at least one fluid cylinder causes said piston to move outwardly, thereby pushing the bracket upward, thereby creating tension on the pad eye, thereby testing the integrity of the weld.

2. The apparatus of claim 1 further including;

at least two opposing arms;

said arms being attached substantially medially to each other in the shape of an "X";

said arms having upper ends and lower ends;

at least one base;
at least one of said lower ends of said arms being attached to said pad eye;
at least one of said lower ends of said arms being attached to said base;
at least one fluid containing cylinder;
said fluid containing cylinder being attached between said upper ends of said arms;
whereby moving fluid into said at least one fluid cylinder causes said piston to move outwardly, thereby pushing the arm outward in a reverse-scissoring motion, thereby creating tension on the pad eye, thereby testing the integrity of the weld.

3. The apparatus in claim 1, further including:
a plurality of arms having top and bottom ends;
said arms being held via at least one hinge on the top ends;
said arms being releasably connected to at least one pad eye at said bottom end of each arm;
said arms being connected to at least one other arm via a fluid containing cylinder;
whereby moving fluid into the cylinder causes the piston to move outwardly to create tension on the pad eye, thereby testing the integrity of the weld.

4. The apparatus in claim 3, wherein said arms can be curved.

5. The apparatus in claim 3, wherein said arms can be angled.

6. The apparatus of claim 1, wherein the cylinder further comprises:
a first end and a second end;
a substantially cylindrical piston carried in said cylinder for movement therein along an axis, of said cylinder, being substantially perpendicular to a plane formed between a pad eye or any device to be tested and a weld attaching said pad eye or the device to be tested to a base;
a shaft, having a first end and a second end, the first end fixedly attached to said internal piston and said second end is fixedly attached to at least one of said arms; and
first and second pressurized fluid attachment apparatus;
wherein said first pressurized fluid attachment apparatus is disposed axially between said cylinder first end and said piston;
wherein said second pressurized fluid attachment apparatus is disposed axially between said cylinder second end and said piston; and
wherein pressurized fluid enters said cylinder through said first attachment apparatus or said second attachment apparatus.

7. The apparatus of claim 6, wherein said cylinder comprises:
said second end of said shaft is fixedly attached to at least one of said arms.

8. The apparatus in claim 1, further including:
a support column with a bottom and top end;
a support bar which is releasably attached to said pad eye;
said support bar being releasably attached to said support column;
a bridge plate or cross bar;
said support column being releasably attached to said bridge plate or column;
at least two fluid containing cylinders;
said cylinders being attached to said bridge plate or cross bar;
a base;
said cylinders also being attached to the base;
whereby moving fluid into the cylinder causes the piston to move outwardly,
thereby pushing the bridge plate and support column upward, this will also cause said bar to move upward thereby creating tension on the pad eye, thereby testing the integrity of the weld.

9. The apparatus of claim 8 whereby;
moving fluid into the cylinder causes the piston to move downwardly, thereby
pulling the bridge plate and support column downward, this will also said bar to move downward thereby creating tension on the pad eye, thereby testing the integrity of the weld.

10. The apparatus of claim 1 whereby;
moving fluid into said at least one fluid cylinder causes said piston to move
inwardly, thereby pulling the bracket downward, thereby creating tension on the pad eye, thereby testing the integrity of the weld.

11. The apparatus of claim 1 whereby,
said clamp is attached to a beam.

12. The apparatus of claim 1 whereby,
said clamp is attached to a pole.

13. The apparatus of claim 2 whereby;
moving fluid into said at least one fluid cylinder causes said piston to move
inwardly, thereby pulling the arm outward in a scissoring motion, thereby creating tension on the pad eye, thereby testing the integrity of the weld.

14. A method for testing weld strength and integrity of an attachment weld when desired comprising the steps of:
providing a desired test piece wherein said test piece comprises a pad eye,
lifting lug, or other device being tested;
providing a framework including at least two pieces;
providing at least one fluid cylinder, having a first end and a second end,
mounted with the framework, for moving a piston therein inwardly and outwardly as fluid is moved out or in respectively;
providing a first and second attachment apparatus, wherein a pressurized fluid
can enter in or exhaust from said cylinder;
providing an attachment structure for attaching to said test piece;
providing said mounted framework; and
assembling the framework with the mounted cylinder fixedly attached on the
mounted framework;
whereby urging fluid into the cylinder causes the piston to move outwardly to
tension the pad eye thus testing the integrity of the weld, and
whereby the testing technician or test operator can inspect the tested device
and the weld for any structural damage or deformation.

15. The method as in claim 14, whereby urging fluid into the cylinder causes the piston to move inwardly to tension the test piece thus testing the integrity of the weld.

16. The method as in claim 14, further providing said mounted framework with;
a plurality of arms having top and bottom ends;
attaching said arms via at least one hinge on the top ends;
releasably connecting said arms to at least one pad eye at said bottom end of
each arm;

releasably connecting said arms to at least one other arm via a fluid containing
cylinder;
moving fluid into the cylinder to cause the piston to move outwardly to create tension on the pad eye, thereby testing the integrity of the weld.

17. The method of claim 16 whereby;
moving fluid into the cylinder to cause the piston to move inwardly to create
tension on the pad eye, thereby testing the integrity of the weld.

18. The method as in claim 14, further providing said mounted framework with;
a support column with a bottom and top end;
releasably attaching a support bar to said pad eye;
releasably attaching said support bar to said support column;
providing a bridge plate or cross bar;
releasably attaching said support column to said bridge plate or cross bar;
providing at least two fluid containing cylinders;
attaching said cylinders to said bridge plate or column;
providing a base;
attaching said cylinders to said base;
moving fluid into the cylinder causing said piston to move outwardly, thereby
pushing the bridge plate and support column upward, also causing said bar to move upward thereby creating tension on the pad eye, thereby testing the integrity of the weld.

19. The method of claim 18 whereby;
moving fluid into the cylinder causes the piston to move downwardly, thereby
pulling the bridge plate and support column downward, also causing said bar to move downward thereby creating tension on the pad eye, thereby testing the integrity of the weld.

20. The method of claim 14, further providing;
a base;
attaching a clamp to said base;
attaching at least one fluid containing cylinder to said clamp;
providing at least one bracket;
releasably attaching said at least one bracket to said pad eye;
moving fluid into said at least one fluid cylinder causing said piston to move
outwardly, thereby pushing the bracket upward, thereby creating tension on the pad eye, thereby testing the integrity of the weld.

21. The method of claim 20 whereby;
moving fluid into said at least one fluid cylinder causes said piston to move
inwardly, thereby pulling the bracket downward, thereby creating tension on the pad eye, thereby testing the integrity of the weld.

22. The method of claim 20 providing,
attaching said clamp to a beam.

23. The method of claim 20 providing,
attaching said clamp to a pole.

24. The method of claim 14, further including;
providing at least two opposing arms;
attaching said arms substantially medially to each other in the shape of an "X";
providing said arms with upper ends and lower ends;
providing at least one base;

attaching at least one of said lower ends of said arms to said pad eye;
attaching at least one of said lower ends of said arms to said base;
providing at least one fluid containing cylinder;
attaching said fluid containing cylinder between said upper ends of said arms;
moving fluid into said at least one fluid cylinder causing said piston to move
outwardly, thereby pushing the arm outward in a reverse-scissoring motion, thereby creating tension on the pad eye, thereby testing the integrity of the weld.

25. The method of claim 24 whereby;
moving fluid into said at least one fluid cylinder causing said piston to move
inwardly, thereby pulling the arm outward in a scissoring motion, thereby creating tension on the pad eye, thereby testing the integrity of the weld.

26. The method as in claim 14, further including calculating a required cylinder test pressure, comprising the steps of:
determining a required test load based on the weight to be supported by the
test piece;
determining an effective area of the cylinder piston;
dividing said test load by the effective area of the cylinder piston;
assembling the framework with the mounted cylinder fixedly attached at the
first end of said cylinder to said test piece;
retracting the cylinder shaft thereby exerting a force substantially
perpendicular to a plane formed between a pad eye or other lifting lug being tested and a weld attaching said pad eye or lifting lug to a base and away from said test piece;
increasing said substantially perpendicular force by increasing the pressure of
the pressurized fluid in the cylinder;
increasing said pressure until the calculated required pressure is reached; and
inspecting the test piece and its attachment weld for any structural damage or deformation.

27. A method for testing the strength and integrity of an attachment weld when
desired with a single cylinder apparatus comprising the steps of:
providing at least one desired test piece;
providing a framework including at least two pieces;
mounting said single cylinder to the framework, said cylinder having a first
end, a second end, and a piston therein, wherein said piston moves inwardly and outwardly as fluid is moved out of or into said cylinder respectively;
mounting said framework about said at least one desired test piece;
assembling the framework with said at least one mounted cylinder fixedly attached at one end of said cylinder to said desired test piece;
retracting the cylinder shaft thereby exerting a force substantially
perpendicular to a plane formed between said desired test piece, being tested, and a base and in a direction away from said test piece;

increasing said substantially perpendicular force by increasing the pressure of
the fluid in the cylinder;
increasing said pressure until a pre-calculated required pressure is reached; and
inspecting the test piece for damage or deformation.

28. The method as in claim 27 wherein said test piece comprises pad eye, lifting lug, or other device to be tested.

29. A method for non-destructively testing strength and integrity of a structure with a multiple cylinder test apparatus comprising the steps of:
providing at least one desired test piece;
providing a framework including at least two pieces; wherein said base may
be a part of said desired test piece;
mounting a plurality of fluid cylinders to the framework, said plurality of fluid
cylinders each having a first end, a second end, and a piston therein, wherein said pistons each moving inwardly and outwardly as fluid is moved out of or into said plurality of fluid cylinders respectively;
mounting said framework about said at least one desired test piece;
assembling the framework with said plurality of fluid cylinders each fixedly
attached at said first end of each said plurality of fluid cylinders to said base and at said second end to a cross bar;
extending the cylinder shafts thereby exerting a force substantially
perpendicular to and toward said cross bar;
transferring said force from said cross bar to a support beam which is attached
to said desired test piece;
transferring said force from said support beam to said desired test piece;
increasing said force by increasing the pressure of the fluid in the cylinder;
increasing the pressure until a pre-calculated required pressure is reached, wherein said pre-calculated required pressure produces a force which is below the rated strength of the test piece; and
inspecting the test piece for damage or deformation.

30. A method for non-destructively testing the strength and integrity of a test piece having first and second parts, which comprises:
anchoring the first part of the test piece;
attaching a piston from a hydraulic cylinder to the second part of the test piece;
moving the piston to put the test piece under tension, wherein the load produced under the tension is below the rated strength of the test piece; and
inspecting the test piece for damage.

31. The method according to claim 30, wherein said test piece is a pad eye.

* * * * *

(12) EX PARTE REEXAMINATION CERTIFICATE (10473rd)
United States Patent
Scarborough

(10) Number: US 7,284,447 C1
(45) Certificate Issued: *Jan. 13, 2015

(54) APPARATUS AND METHOD FOR TESTING WELD INTEGRITY

(75) Inventor: Randall L. Scarborough, Carencrow, LA (US)

(73) Assignee: Randall L. Scarborough, Carencro, LA (US)

Reexamination Request:
No. 90/012,842, Apr. 15, 2013

Reexamination Certificate for:
Patent No.: 7,284,447
Issued: Oct. 23, 2007
Appl. No.: 11/047,127
Filed: Jan. 31, 2005

(*) Notice: This patent is subject to a terminal disclaimer.

Related U.S. Application Data

(63) Continuation-in-part of application No. 10/365,105, filed on Feb. 12, 2003, now Pat. No. 6,848,322.

(51) Int. Cl.
*G01N 3/20* (2006.01)

(52) U.S. Cl.
USPC ............................................................ 73/850

(58) Field of Classification Search
None
See application file for complete search history.

(56) References Cited

To view the complete listing of prior art documents cited during the proceeding for Reexamination Control Number 90/012,842, please refer to the USPTO's public Patent Application Information Retrieval (PAIR) system under the Display References tab.

*Primary Examiner* — Tuan H Nguyen

(57) ABSTRACT

An apparatus and method for testing weld integrity is disclosed which is portable, self-contained, adaptable for field use in most locations, and can verify the integrity of attachment welds. The testing apparatus includes a cylinder or cylinders, attachable to the desired object to be tested on one end and to a cross bar on the other end, support beam or beams which, along with the cylinder or cylinders, support the test apparatus, a supply for pressurized fluid, and a control manifold for flow direction and pressure measurement. The pressurized fluid moves the cylinder shaft creating a load on the test piece. As the fluid pressure increases, the cylinder shafts extend or retract and exert a required load on the test piece. The test piece is then inspected for breakage or damage such as deformation or attachment weld cracking.

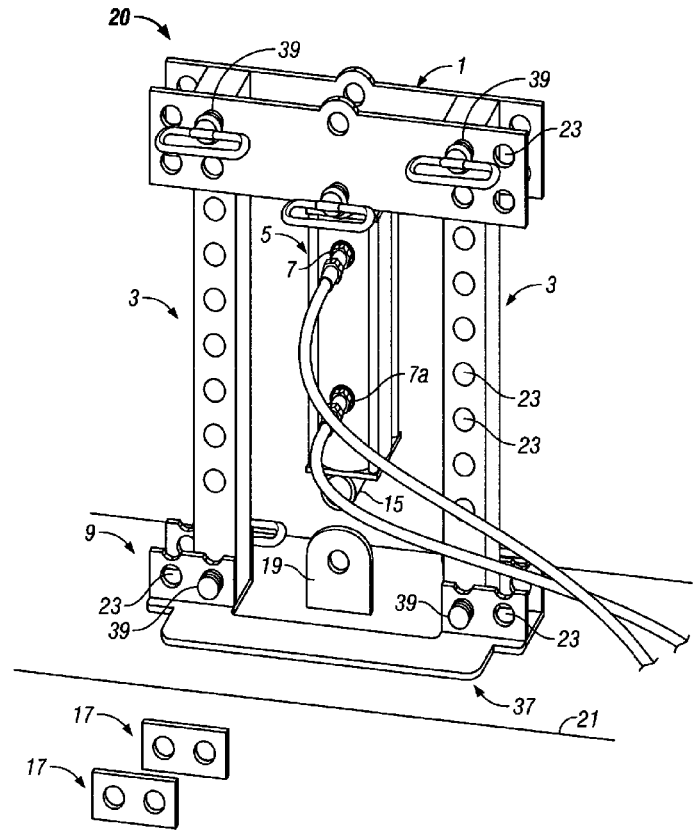

US 7,284,447 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 29 is cancelled.

Claims 1, 14, 15 and 27 are determined to be patentable as amended.

Claims 2-13, 16-26, 28 and 30-31 were not reexamined.

1. An apparatus for non-destructively testing [the] weld strength and integrity of at least one *attachment* weld [when desired], comprising:
 a framework including at least two pieces;
 at least one fluid containing cylinder, for moving a piston therein inwardly and outwardly as fluid is moved out of or into the *at least one fluid containing* cylinder, respectively;
 an attachment structure for attaching to a pad eye or [any] *other* device [to be tested] *joined by the at least one attachment weld to another structure*;
 a base;
 said base including a clamp;
 said at least one fluid containing cylinder attached to said clamp;
 at least one bracket; and
 said at least one bracket being releasably attached to said pad eye *or other device*;
 whereby moving fluid into said at least one fluid cylinder causes said piston to move outwardly, thereby pushing the *at least one* bracket upward, thereby creating tension on the pad eye[.] *or other device*, thereby testing the integrity of the *at least one attachment* weld.

14. A method for testing weld strength and integrity of an attachment weld [when desired], comprising the steps of:
 providing [a desired test piece wherein said test piece comprises] *the attachment weld joining* a pad eye, lifting lug, or other device [being tested] *to another structure*;
 providing a framework including at least two pieces;
 providing at least one fluid cylinder, having a first end and a second end, mounted with the framework *to produce a mounted cylinder within a mounted framework*, for moving a piston therein inwardly and outwardly as fluid is moved out or in respectively;
 providing a first and second attachment apparatus, wherein a pressurized fluid can enter in or exhaust from said *at least one fluid* cylinder;
 providing an attachment structure for attaching to said [test piece] *pad eye, lifting lug or other device joined to said another structure by the attachment weld*; and
 [providing said mounted framework; and]
 assembling the framework with the mounted cylinder fixedly attached on the mounted framework;
 [whereby] urging fluid into the cylinder [causes] *to cause* the piston to move outwardly to tension the pad eye, *lifting lug or other device joined to said another structure*, thus testing the integrity of the *attachment* weld, and
 whereby [the] *a* testing technician or test operator can inspect the [tested device and the weld] *attachment weld* for any structural damage or deformation.

15. The method as in claim 14, whereby *the* urging fluid into the *at least one fluid* cylinder causes the piston to move inwardly to tension the [test piece] *pad eye, lifting lug or other device*, thus testing the integrity of the *attachment* weld.

27. A method for testing [the] strength and integrity of an attachment weld [when desired] with a single cylinder apparatus comprising the steps of:
 providing at least one [desired] test piece *comprising a pad eye and the attachment weld joining the pad eye to another structure*;
 providing a framework including at least two pieces;
 mounting said single cylinder *apparatus* to the framework, said *single* cylinder *apparatus* having a first end, a second end, and a piston therein, wherein said piston moves inwardly and outwardly as fluid is moved out of or into said *single* cylinder *apparatus* respectively;
 mounting said framework about said at least one [desired] test piece;
 assembling the framework with said [at least one mounted] *single* cylinder *apparatus* fixedly attached at one end of said *single* cylinder *apparatus* to said [desired] *at least one* test piece;
 retracting [the] *a* cylinder shaft *of the single cylinder apparatus*, thereby exerting a force substantially perpendicular to a plane formed between said [desired] *pad eye of the at least one* test piece[, being tested,] and a base and in a direction away from said *pad eye of said at least one* test piece;
 increasing said substantially perpendicular force by increasing the pressure of the fluid in the cylinder;
 increasing [said] pressure until a pre-calculated, required pressure is reached; and
 inspecting the *at least one* test piece for damage or deformation.

\* \* \* \* \*